United States Patent
Walsh et al.

(10) Patent No.: US 8,867,041 B2
(45) Date of Patent: Oct. 21, 2014

(54) OPTICAL VACUUM ULTRA-VIOLET WAVELENGTH NANOIMPRINT METROLOGY

(75) Inventors: Phillip Walsh, Austin, TX (US); Jeffrey B. Hurst, Cedar Park, TX (US); Dale A. Harrison, Austin, TX (US)

(73) Assignee: Jordan Valley Semiconductor Ltd, Nigdal Haemek (IL)

( * ) Notice: Subject to any disclaimer, the term of this patent is extended or adjusted under 35 U.S.C. 154(b) by 302 days.

(21) Appl. No.: 13/350,780

(22) Filed: Jan. 15, 2012

(65) Prior Publication Data
US 2012/0182542 A1 Jul. 19, 2012

Related U.S. Application Data

(60) Provisional application No. 61/433,526, filed on Jan. 18, 2011.

(51) Int. Cl.
*G01N 21/55* (2014.01)
*G03F 7/00* (2006.01)
*G01N 21/956* (2006.01)

(52) U.S. Cl.
CPC ............ *G03F 7/0002* (2013.01); *G01N 21/956* (2013.01)
USPC ............................ 356/448; 356/369; 356/601

(58) Field of Classification Search
CPC .... G01N 21/95; G01N 21/956; G03F 1/0092; G03F 7/0002
USPC ............ 356/51, 369, 612, 364, 445, 448, 601
See application file for complete search history.

(56) References Cited

U.S. PATENT DOCUMENTS 3,091,154 A 5/1963 Hall
3,160,752 A 12/1964 Bennett
(Continued)

FOREIGN PATENT DOCUMENTS

CN 2430682 Y 5/2001
JP H08-022129 A 1/1996
(Continued)

OTHER PUBLICATIONS

U.S. Appl. No. 12/590,151 Official Action dated Jun. 25, 2010.
(Continued)

*Primary Examiner* — Tarifur Chowdury
*Assistant Examiner* — Michael P Lapage
(74) *Attorney, Agent, or Firm* — D. Kligler I.P. Services Ltd.

(57) ABSTRACT

An optical metrology apparatus for measuring nanoimprint structures using Vacuum Ultra-Violet (VUV) light is described. Focusing optics focus light onto the sample and collect the light reflected from the sample so as to record an optical response from nanoimprint structures on the sample, wherein the nanoimprint structures have an orientation that varies over a surface of the sample. A sample stage is configured to support the sample. At least one computer is connected to the metrology instrument and the sample stage and is configured to run a computer program which causes the sample stage to rotate the sample so as to present multiple different locations on the sample to the optical metrology instrument such that the orientation of the nanoimprint structures at the multiple different locations remains fixed with respect to a plane of the focusing optics of the metrology instrument in order to eliminate polarization effects.

14 Claims, 25 Drawing Sheets

(56) References Cited

U.S. PATENT DOCUMENTS

| | | |
|---|---|---|
| 3,572,951 A | 3/1971 | Rothwarf et al. |
| 3,751,643 A | 8/1973 | Dill et al. |
| 3,825,347 A | 7/1974 | Kaiser |
| 4,029,419 A | 6/1977 | Schumann et al. |
| 4,040,750 A | 8/1977 | Zwiener |
| 4,368,983 A | 1/1983 | Bennett |
| 4,645,349 A | 2/1987 | Tabata |
| 4,729,657 A | 3/1988 | Cooper et al. |
| 4,837,603 A | 6/1989 | Hayashi |
| 4,899,055 A | 2/1990 | Adams |
| 4,984,894 A | 1/1991 | Kondo |
| 5,042,949 A | 8/1991 | Greenberg et al. |
| 5,045,704 A | 9/1991 | Coates |
| 5,120,966 A | 6/1992 | Kondo |
| 5,128,549 A | 7/1992 | Kaya |
| 5,164,790 A | 11/1992 | McNeil et al. |
| 5,182,618 A | 1/1993 | Heinonen |
| 5,241,366 A | 8/1993 | Bevis et al. |
| 5,251,006 A | 10/1993 | Honigs et al. |
| 5,357,448 A | 10/1994 | Stanford |
| RE34,783 E | 11/1994 | Coates |
| 5,388,909 A | 2/1995 | Johnson et al. |
| 5,432,607 A | 7/1995 | Taubenblatt |
| 5,440,141 A | 8/1995 | Horie |
| 5,452,091 A | 9/1995 | Johnson |
| 5,486,701 A | 1/1996 | Norton et al. |
| 5,493,401 A | 2/1996 | Horie et al. |
| 5,581,350 A | 12/1996 | Chen et al. |
| 5,607,800 A | 3/1997 | Ziger |
| 5,608,526 A | 3/1997 | Piwonka-Corle et al. |
| 5,686,993 A | 11/1997 | Kokubo et al. |
| 5,703,692 A | 12/1997 | McNeil et al. |
| 5,739,909 A | 4/1998 | Blayo et al. |
| 5,747,813 A | 5/1998 | Norton et al. |
| 5,754,296 A | 5/1998 | Law |
| 5,771,094 A | 6/1998 | Carter |
| 5,777,733 A | 7/1998 | Radziuk |
| 5,781,304 A | 7/1998 | Kotidis et al. |
| 5,784,167 A | 7/1998 | Ho |
| 5,798,837 A | 8/1998 | Aspnes et al. |
| 5,805,285 A | 9/1998 | Johs et al. |
| 5,835,225 A | 11/1998 | Thakur |
| 5,867,276 A | 2/1999 | McNeil et al. |
| 5,880,831 A | 3/1999 | Buermann et al. |
| 5,900,939 A | 5/1999 | Aspnes et al. |
| 5,903,351 A | 5/1999 | Jeong et al. |
| 5,917,594 A | 6/1999 | Norton |
| 5,963,329 A | 10/1999 | Conrad et al. |
| 5,991,022 A | 11/1999 | Buermann et al. |
| 6,052,401 A | 4/2000 | Wieser et al. |
| 6,091,485 A | 7/2000 | Li et al. |
| 6,122,052 A | 9/2000 | Barnes et al. |
| 6,128,085 A | 10/2000 | Buermann et al. |
| 6,129,807 A | 10/2000 | Grimbergen et al. |
| 6,181,427 B1 | 1/2001 | Yarussi et al. |
| 6,184,529 B1 | 2/2001 | Contini |
| 6,184,984 B1 | 2/2001 | Lee et al. |
| 6,222,199 B1 | 4/2001 | Freeouf |
| 6,226,086 B1 | 5/2001 | Holbrook et al. |
| 6,261,853 B1 | 7/2001 | Howell et al. |
| 6,265,033 B1 | 7/2001 | Hilliard |
| 6,275,292 B1 | 8/2001 | Thakur et al. |
| 6,278,519 B1 | 8/2001 | Rosencwaig et al. |
| 6,281,674 B1 | 8/2001 | Huang |
| 6,297,880 B1 | 10/2001 | Rosencwaig et al. |
| 6,304,326 B1 | 10/2001 | Aspnes et al. |
| 6,313,466 B1 | 11/2001 | Olsen et al. |
| 6,323,947 B1 | 11/2001 | Freeouf |
| 6,327,035 B1 | 12/2001 | Li et al. |
| 6,340,602 B1 | 1/2002 | Johnson et al. |
| 6,361,646 B1 | 3/2002 | Bibby, Jr. et al. |
| 6,392,756 B1 | 5/2002 | Li et al. |
| 6,411,385 B2 | 6/2002 | Aspnes et al. |
| 6,414,302 B1 | 7/2002 | Freeouf |
| 6,417,921 B2 | 7/2002 | Rosencwaig et al. |
| 6,433,878 B1 | 8/2002 | Niu et al. |
| 6,453,006 B1 | 9/2002 | Koppel et al. |
| 6,483,580 B1 | 11/2002 | Xu et al. |
| 6,485,872 B1 | 11/2002 | Rosenthal et al. |
| 6,525,829 B1 | 2/2003 | Powell et al. |
| 6,538,731 B2 | 3/2003 | Niu et al. |
| 6,549,279 B2 | 4/2003 | Adams et al. |
| 6,556,303 B1 | 4/2003 | Rangarajan et al. |
| 6,572,951 B2 | 6/2003 | Hasegawa et al. |
| 6,580,510 B2 | 6/2003 | Nawracala |
| 6,590,656 B2 | 7/2003 | Xu et al. |
| 6,608,690 B2 | 8/2003 | Niu et al. |
| 6,630,673 B2 | 10/2003 | Khalil et al. |
| 6,630,996 B2 | 10/2003 | Rao et al. |
| 6,633,831 B2 | 10/2003 | Nikoonahad et al. |
| 6,643,354 B2 | 11/2003 | Koppel et al. |
| 6,654,131 B2 | 11/2003 | Opsal et al. |
| 6,657,736 B1 | 12/2003 | Finarov et al. |
| 6,657,737 B2 | 12/2003 | Kimba et al. |
| 6,665,075 B2 | 12/2003 | Mittleman et al. |
| 6,673,637 B2 | 1/2004 | Wack et al. |
| 6,704,661 B1 | 3/2004 | Opsal et al. |
| 6,710,865 B2 | 3/2004 | Forouhi et al. |
| 6,713,753 B1 | 3/2004 | Rovira et al. |
| 6,713,775 B2 | 3/2004 | Chelvayohan et al. |
| 6,721,052 B2 | 4/2004 | Zhao et al. |
| 6,734,968 B1 | 5/2004 | Wang et al. |
| 6,765,676 B1 | 7/2004 | Buermann |
| 6,768,785 B2 | 7/2004 | Koppel |
| 6,768,967 B2 | 7/2004 | Johnson et al. |
| 6,775,015 B2 | 8/2004 | Bischoff et al. |
| 6,778,273 B2 | 8/2004 | Norton et al. |
| 6,778,911 B2 | 8/2004 | Opsal et al. |
| 6,801,309 B1 | 10/2004 | Nelson |
| 6,806,951 B2 | 10/2004 | Wack et al. |
| 6,806,971 B2 | 10/2004 | Finarov |
| 6,813,034 B2 | 11/2004 | Rosenewaig et al. |
| 6,819,426 B2 | 11/2004 | Sezginer et al. |
| 6,856,408 B2 | 2/2005 | Raymon |
| 6,879,395 B2 | 4/2005 | Oka et al. |
| 6,891,626 B2 | 5/2005 | Niu et al. |
| 6,897,456 B2 | 5/2005 | Hasegawa et al. |
| 6,897,807 B2 | 5/2005 | Kishigami et al. |
| 6,898,537 B1 | 5/2005 | McGahan |
| 6,909,507 B2 | 6/2005 | Norton et al. |
| 6,917,419 B2 | 7/2005 | Fielden et al. |
| 6,919,957 B2 | 7/2005 | Nikoonahad et al. |
| 6,934,025 B2 | 8/2005 | Opsal et al. |
| 6,979,578 B2 | 12/2005 | Venugopal |
| 6,982,792 B1 | 1/2006 | Woollam et al. |
| 6,987,832 B2 | 1/2006 | Koppel et al. |
| 7,006,235 B2 | 2/2006 | Levy et al. |
| 7,026,165 B2 | 4/2006 | DeGrandpre |
| 7,026,626 B2 | 4/2006 | Harrison |
| 7,030,999 B2 | 4/2006 | Bischoff et al. |
| 7,031,894 B2 | 4/2006 | Niu et al. |
| 7,046,375 B2 | 5/2006 | Bischoff et al. |
| 7,049,156 B2 | 5/2006 | Kueny |
| 7,053,991 B2 | 5/2006 | Sandusky |
| 7,061,614 B2 | 6/2006 | Wang et al. |
| 7,067,818 B2 | 6/2006 | Harrison |
| 7,068,363 B2 | 6/2006 | Bevis et al. |
| 7,072,050 B2 | 7/2006 | Kimba et al. |
| 7,095,511 B2 | 8/2006 | Chalmers et al. |
| 7,126,131 B2 | 10/2006 | Harrison |
| 7,130,029 B2 | 10/2006 | Wack et al. |
| 7,189,973 B2 | 3/2007 | Harrison |
| 7,196,785 B2 | 3/2007 | Nishiyama et al. |
| 7,224,471 B2 | 5/2007 | Bischoff et al. |
| 7,242,477 B2 | 7/2007 | Mieher et al. |
| 7,271,394 B2 | 9/2007 | Harrison |
| 7,282,703 B2 | 10/2007 | Walsh et al. |
| 7,342,235 B1 | 3/2008 | Harrison et al. |
| 7,349,079 B2 | 3/2008 | Zhao et al. |
| 7,359,052 B2 | 4/2008 | Fielden et al. |
| 7,391,030 B2 | 6/2008 | Harrison |
| 7,391,524 B1 | 6/2008 | Chen et al. |
| 7,394,551 B2 | 7/2008 | Harrison |
| 7,399,975 B2 | 7/2008 | Harrison |

(56) References Cited

U.S. PATENT DOCUMENTS

| | | | |
|---|---|---|---|
| 7,446,876 | B2 | 11/2008 | Harrison |
| 7,485,869 | B2 | 2/2009 | Harrison et al. |
| 7,511,265 | B2 | 3/2009 | Walsh et al. |
| 7,579,601 | B2 | 8/2009 | Harrison et al. |
| 7,622,310 | B2 | 11/2009 | Harrison et al. |
| 7,643,666 | B2 | 1/2010 | Setija et al. |
| 7,663,097 | B2 | 2/2010 | Walsh et al. |
| 7,663,747 | B2 | 2/2010 | Harrison et al. |
| 7,684,037 | B2 | 3/2010 | Harrison |
| 7,804,057 | B2 | 9/2010 | Sato et al. |
| 7,804,059 | B2 | 9/2010 | Harrison |
| 7,948,631 | B2 | 5/2011 | Walsh |
| 7,990,549 | B2 | 8/2011 | Walsh |
| 8,014,000 | B2 | 9/2011 | Harrison |
| 8,054,453 | B2 | 11/2011 | Harrison |
| 8,119,991 | B2 | 2/2012 | Harrison |
| 8,153,987 | B2 | 4/2012 | Hurst et al. |
| 2001/0055118 | A1 | 12/2001 | Nawracala |
| 2002/0030826 | A1 | 3/2002 | Chalmers et al. |
| 2002/0088952 | A1 | 7/2002 | Rao et al. |
| 2002/0126277 | A1 | 9/2002 | Norton et al. |
| 2002/0149774 | A1 | 10/2002 | McAninch |
| 2002/0154302 | A1 | 10/2002 | Rosencwaig et al. |
| 2002/0190207 | A1 | 12/2002 | Levy et al. |
| 2003/0071996 | A1 | 4/2003 | Wang et al. |
| 2003/0081201 | A1 | 5/2003 | Shibata et al. |
| 2004/0150820 | A1 | 8/2004 | Nikoonahad et al. |
| 2005/0001172 | A1 | 1/2005 | Harrison |
| 2005/0036143 | A1 | 2/2005 | Huang |
| 2006/0001885 | A1 | 1/2006 | Hertzsch et al. |
| 2006/0033921 | A1* | 2/2006 | Den Boef et al. ............ 356/446 |
| 2006/0066855 | A1 | 3/2006 | Boef et al. |
| 2007/0181793 | A1 | 8/2007 | Harrison |
| 2007/0215801 | A1 | 9/2007 | Walsh et al. |
| 2008/0129986 | A1 | 6/2008 | Walsh |
| 2008/0181793 | A1 | 7/2008 | Mistry et al. |
| 2008/0246951 | A1 | 10/2008 | Walsh et al. |
| 2009/0002711 | A1 | 1/2009 | Harrison |
| 2009/0248074 | A1 | 10/2009 | Kliegman et al. |
| 2010/0051822 | A1 | 3/2010 | Harrison |
| 2010/0277741 | A1 | 11/2010 | Walsh |
| 2010/0290033 | A1 | 11/2010 | Walsh |
| 2012/0170021 | A1 | 7/2012 | Walsh |
| 2012/0275568 | A1* | 11/2012 | Mazor et al. .................. 378/88 |

FOREIGN PATENT DOCUMENTS

| | | | |
|---|---|---|---|
| JP | 10160572 | A | 6/1998 |
| JP | 2000205966 | A | 7/2000 |
| JP | 2000249600 | A | 9/2000 |
| JP | 2002243381 | A | 8/2002 |
| JP | 2003202266 | A | 7/2003 |
| JP | 2003232681 | A | 8/2003 |
| WO | 9902970 | A1 | 1/1999 |
| WO | 2007126612 | A2 | 11/2007 |
| WO | 2007130295 | A2 | 11/2007 |

OTHER PUBLICATIONS

U.S. Appl. No. 12/844,851 Official Action dated Oct. 17, 2012.
U.S. Appl. No. 12/876,242 Official Action dated Nov. 19, 2010.
Hofemann, P., "From Possible to Practical—The Evolution of Nanoimprint for Patterned Media", session 6, IDEMA DISKCON Asia-Pacific conference, Singapore, Mar. 12-13, 2009.
Al-Assaad et al., "Characterizing Nanoimprint Profile Shape and Polymer Flow Behavior using Visible Light Angular Scatterometry", Journal of Vacuum Science & Technology B: Microelectronics and Nanometer Structures, vol. 25, issue 6, pp. 2396-2401, Nov. 2007.
Patrick et al., "Scatterometry for in situ measurement of pattern reflow in nanoimprinted polymers", Applied Physics Letters, vol. 93, issue 23, 233105/1-233105/3, Dec. 2008.
Bloomer, I., "Templates, DTR and BPM Media", session 7, IDEMA DISKCON Asia-Pacific conference, Singapore, Mar. 12-13, 2009.
Terry Jr, F. L., "Accuracy limitations in specular-mode optical topography extraction", Proceedings of the SPIE, vol. 5038, pp. 547-558, May 27, 2003.
U.S. Appl. No. 12/590,151 Official Action dated Mar. 17, 2011.
U.S. Appl. No. 12/834,939 Official Action dated Jun. 10, 2011.
U.S. Appl. No. 12/876,242 Official Action dated May 20, 2011.
JP Patent Application # 528098/06 Official Action dated Aug. 30, 2011.
U.S. Appl. No. 12/854,917 Official Action dated Jul. 28, 2011.
U.S. Appl. No. 12/454,837 Official Action dated Oct. 3, 2011.
U.S. Appl. No. 12/834,939 Official Action dated Oct. 29, 2010.
Das et al., "Image Evaluation of the High-Resolution VUV Spectrometer at SURF II by Ray Tracing", Journal of Research of the National Institute of Standards and Technology, vol. 103, No. 5, pp. 483-495, Sep.-Oct. 1998.
Re-Examination U.S. Appl. No 90/009,409 Official Action dated Jun. 18, 2010.
Chinese Patent Application No. 200480027513.6 Official Action dated Jul. 18, 2008.
Re-Examination U.S. Appl. No. 90/009,320 Official Action dated Sep. 25, 2009, and Notice of Intent to Issue Re-Exam Certificate dated Jun. 23, 2010.
Aspnes, D.E., "Determination of Optical Properties by Ellipsometry", Handbook of Optical Constants of Solids, vol. 1, pp. 104-108, Academic Press, 1998.
Bloomstein et al., "Contamination Rates of Optical Surface at 157nm in the Presence of Hydrocarbon Impurities", Optical Microlithography XV, Proceedings of the SPIE, vol. 4691, pp. 709-723, Jul. 30, 2002.
Field et al., "Method of Using the Reflectance Ratios of Difference Angles of Incidence for the Determination of Optical Constants", Applied Optics, vol. 10, No. 6, pp. 1402-1405, Jun. 1971.
Hunter, W., "Errors in Using the Reflectance vs Angle of Incidence Method for Measuring Optical Constants", Journal of the Optical Society of America, vol. 55, No. 10, part 1, pp. 1197-1204, Oct. 1965.
Hunter et al., "Thickness of Absorbing Films Necessary to Measure Their Optical Constants Using the Reflectance-Vs-Angle-of-Incidence Method", Journal of the Optical Society of America, vol. 64, No. 4, pp. 429-433, Apr. 1974.
Jellison et al., "Parameterization of the Optical Functions of Amorphous Materials in the Interband Region", Applied Physics Letter, Jul. 15, 1996 (vol. 69, No. 3, pp. 371-373), and Sep. 30, 1996 (vol. 69, No. 14, p. 2137).
Okoroanyanwu et al., "Contamination Monitoring and Control on ASML MS-VII 157nm Exposure Tool", Optical Microlithography XVII, Proceedings of the SPIE, vol. 5377, pp. 1695-1707, May 28, 2004.
International Application PCT/US2004/030859 Search Report dated Feb. 24, 2005.
Rivas, C., "Optical Characterization of Hafnium-Based High-K Dielectric Films Using Vacuum Ultraviolet Reflectometry", Proceedings of the XV International Conference on Vacuum Ultraviolet Radiation Physics, Berlin, Germany Jul. 29-Aug. 3, 2007.
International Application PCT/US2007/010003 Search Report issued Dec. 17, 2008.
U.S. Appl. No. 10/930,339 Official Action dated Sep. 29, 2009.
U.S. Appl. No. 10/930,339 Official Action dated Jan. 18, 2007.
U.S. Appl. No. 10/930,339 Official Action dated Sep. 6, 2007.
U.S. Appl. No. 10/930,339 Official Action dated Apr. 18, 2008.
U.S. Appl. No. 10/930,339 Official Action dated Nov. 13, 2008.
Moharam et al.., "Stable Implementation of the Rigorous Coupled-Wave Analysis for Surface-Relief Gratings: Enhanced Transmittance Matrix Approach", Optical Society of America, vol. 12, No. 5, pp. 1077-1086, May 1995.
Visentine, J., "Optical Characterization of Molecular Contaminant Films", Photonics Tech Briefs, Jan. 1, 2007.
U.S. Appl. No. 12/592,641 Official Action dated Aug. 20, 2010.
Japanese Patent Application # 528098/06 Official Action dated Jun. 15, 2010 (including English translation).
Re-Examination U.S. Appl. No. 95/000,535 Official Action dated May 14, 2010.

(56) References Cited

OTHER PUBLICATIONS

Acton Research Corporation, "Acton Research Purged CAMS Optical Measurement System", Acton Research Product Brochure, USA, Published prior to Sep. 23, 2003.
McPherson Inc., "Reflectometer for Sample Analysis", McPherson Product Brochure, USA, Published prior to Sep. 23, 2003.
McPherson Inc., "Spectral Reflectometer", McPherson Product Brochure, USA, Nov. 12, 2001.
McPherson Inc., "VUVaS Spectrophotometers for 115 nm to >380nm", McPherson Product Brochure, USA, published prior to Sep. 23, 2003.
McPherson Inc., "VUVaS Spectrophotometers, Made to Measure 115-380 nm", McPherson Product Brochure, USA, published prior to Sep. 23, 2003.
Rubloff, G.W., "Surface Reflectance Spectroscopy System", Technical Disclosure, IP.com, May 1, 1977.
Sopra., "SE and GXR combined on the same instrument", printed from www.sopra-sa.com on Feb. 19, 2002.
Sopra., "The Ideal Thin Film Characterization Unit for Development and Pilot Line Environment", printed from www.sopra-sa.com on Feb. 19, 2002.
Sopra., "The Thin Film Tool for Next Generation Lithography at 157 nm", printed from www.sopra-sa.com on Feb. 19, 2002.
Moharam et al., "Formulation for Stable and Efficient Implementation of the Rigorous Coupled-Wave Analysis of Binary Gratings", Optical Society of America, vol. 12, No. 5, pp. 1068-1076, May 1995.
Li, L., "Using Symmetries of Grating Groove Profiles to Reduce Computation Cost of the C Method", Optical Society of America, vol. 24, No. 4, pp. 1085-1096, Apr. 2007.
Sentech Instruments GmbH., "Vacuum UV Spectroscopic Ellipsometers", printed from www.sentech.de on Feb. 20, 2002.
J.A. Woolam Company, "Award Winning VUV-VASE is the latest addition to our line of Spectroscopic Ellipsometers", printed from www.jawoolam.com on Nov. 5, 2002.
Request for Ex Parte Reexamination for US Patent # 7,067,818 filed Feb. 11, 2009.
Request for Ex Parte Reexamination for US Patent # 7,067,818 filed Feb. 12, 2010.
Request for Ex Parte Reexamination for US Patent # 7,026,626 filed Nov. 7, 2008.
Tan, E., "Hybrid-Matrix Algorithm for Rigorous Coupled-Wave Analysis of Multilayered Diffraction Gratings", Journal of Modern Optics, vol. 53, No. 4, pp. 417-428, Mar. 10, 2006.
Lalanne, P., "Improved Formulation of the Coupled-Wave Method for Two-Dimensional Gratings", Optical Society of America, vol. 14, No. 7, Jul. 1997, pp. 1592-1598.
Lalanne, P., "On the Effective Medium Theory of Subwavelength Periodic Structures", Journal of Modern Optics, vol. 43, No. 10, pp. 2063-2085, year 1996.
Kinber et al., "Use of Symmetry in Solving Diffraction Problems", Radio Engineering and Electronic Physics, vol. 16, pp. 581-587, year 1971.
Press et al., "Numerical Recipes in C: 15.5 Non-Linear models", The Art of Scientific Computing, Second Edition, 15.5 Non-Linear models, pp. 681-688, Cambridge University Press 2002.
U.S. Appl. No. 12/080,947 (abandoned) Official Action dated Mar. 30, 2010.
Bai et al., "Group Theoretic Approach to Enhancing the Fourier Method for Crossed Gratings with Square Symmetry", Optical Society of America, vol. 23, No. 3, pp. 572-580, Mar. 2006.
Japanese Patent Application # 2009507685 Office Action dated Apr. 3, 2012.
European Patent Application # 04784655.5 Search dated Jun. 27, 2012.
Bai et al., "Group Theoretic Approach to the Enhancement of the Fourier Method for Crossed Gratings: C2 Symmetry Case", Optical Society of America, vol. 22, No. 4, pp. 654-651, Apr. 2005.
Bai et al., "Reduction of Computation Time for Crossed Gratings Problems: A Group Theoretic Approach", Optical Society of America, vol. 21, No. 10, pp. 1886-1894, Oct. 2004.
Li, L., "Use of Fourier Series in the Analysis of Discontinuous Periodic Structure", Optical Society of America, vol. 13, No. 9, pp. 1870-1876, Sep. 1996.
Granet et al., "Efficient Implementation of the Coupled Wave Method for Metallic Lamellar Gratings in TM Polarization", Optical Society of America, vol. 13, No. 5, pp. 1019-1023, May 1996.
Lalanne et al., "Highly Improved Convergence of the Coupled Wave Method for TM Polarization", Optical Society of America, vol. 13, No. 4, pp. 779-784, Apr. 1996.
Tan, E., "Enhanced R Matrix Algorithms for Multilayered Diffraction Gratings", Applied Optics, vol. 45, No. 20, pp. 4803-4809, Jul. 19, 2006.
Kaplan et al., "Characterization of Bidimensional Gratings by Spectroscopic Ellipsometry and Angle Resolved Mueller Polarimetry", Applied Optics, vol. 43, No. 6, pp. 1233-1240, Feb. 20, 2004.
Novikova et al., "Application of Mueller Polarimetry in Conical Diffraction for Critical Dimension Measurements in Microelectronics", Applied Optics, vol. 45, No. 16, pp. 3688-3697, Jun. 1, 2006.
Bao, J., "An Optical Metrology System for Lithography Process Monitoring and Control", Thesis, University of California at Berkeley, Department of Electrical Engineering and Computer Sciences, 135 pages, Spring 2003.
Coulombe et al., "Ellipsometric—Scatterometry for Sub-01um CD Measurements", SPIE, vol. 3332, pp. 282-2393, year 1998.
Opsal et al., "Fundamental Solutions for Real-Time Optical CD Metrology", SPIE, vol. 4689, pp. 163-176, year 2002.
Bischoff et al., "New Aspects of Optical Scatterometry Applied to Microtechnology", SPIE, vol. 3215, pp. 144-155, year 1997.
Minhas et al., "Towards Sub-01 um CD Measurements Using Scatterometry", SPIE, vol. 2725, pp. 729-739, year 1996.
Bischoff et al., "Single Feature Metrology by Means for Light Scatter Analysis", SPIE, vol. 3050, pp. 574-585, year 1997.
Mills et al., "Spectral Ellipsometry on Patters Wafers", SPIE, vol. 2637, pp. 194-203, year 1995.
Depine et al., "Internal Symmetries in Conical Diffraction from Metallic Gratings", Journal of Modern Optics, vol. 48, No. 8, pp. 1405-1411, year 2001.
Xie et al., "Transmission of Light Through Periodic Arrays of Sub-Wavelength Slits in Metallic Hosts", Optics Express, vol. 14, No. 14, pp. 6400-6413, Jul. 10, 2006.
Robert et al., "Control of the Homogeneity of an Optical Grating by a Neural Characterization", Optical Engineering, vol. 44, No. 3, 5 pages, Mar. 2005.
Boyer et al., "Diffraction Theory: Application of the Fast Fourier Factorization to Cylindrical Devices with Arbitrary Cross Section Lighted in Conical Mounting", Optical Society of America, vol. 23. No. 5, pp. 1146-1158, May 2006.
Cordeiro et al., "Phase Constraint for the Waves Diffracted by Lossless Symmetrical Gratings at Littrow Mount", Optical Society of America, vol. 23, No. 1, pp. 166-171, Jan. 2006.
Robert et al., "Experimental Characterization of Subwavelength Diffraction Gratings by an Inverse-Scattering Neural Method", Optical Society of America, vol. 19, No. 12, pp. 2394-2402, Dec. 2002.
Robert et al., "Characterization of Optical Diffraction Gratings by Use of a Neural Method", Optical Society of America, vol. 19, No. 1, pp. 24-32, Jan. 2002.
Li, L., "Symmetries of Cross-Polarization Diffraction Coefficients of Gratings", Optical Society of America, vol. 17, No. 5, pp. 881-887, May 2000.
Logofatu et al., "Identity of the Cross-Reflection Coefficients for Symmetric Surface-Relief Gratings", Optical Society of America, vol. 16, No. 5, pp. 1108-1114, May 1999.
Zolla et al., "Method of Fictitious Sources as Applied to the Electromagnetic Diffraction of a Plane Wave by a Grating in Conical Diffraction Mounts", Optical Society of America, vol. 13, No. 4, pp. 796-802, Apr. 1996.
Peng et al., "Efficient Implementation of Rigorous Coupled-Wave Analysis for Surface-Relief Gratings", Optical Society of America, vol. 12, No. 5, pp. 1087-1096, May 1995.
Li, L., "Multilayer Modal Method for Diffraction Gratings of Arbitrary Profile, Depth and Permittivity", Optical Society of America, vol. 10, No. 12, pp. 2581-2591, Dec. 1993.

(56) References Cited

OTHER PUBLICATIONS

Li et al., "Convergence of the Coupled-Wave Method for Metallic Lamellar Diffraction Gratings", Optical Society of America, vol. 10, No. 6, pp. 1184-1189, Jun. 1993.

Peng, S., "Rigorous Formulation of Scattering and Guidance by Dielectric Grating Waveguides: General Case of Oblique Incidence", Optical Society of America, vol. 6, No. 12, pp. 1869-1883, Dec. 1989.

Moharam et al., "Rigorous Coupled-Wave Analysis of Grating Diffraction-E-mode Polarization and Losses", Optical Society of America, vol. 73, No. 4, pp. 451-455, Apr. 1983.

Moharam et al., "Diffraction Analysis of Dielectric Surface-Relief Gratings", Optical Society of America, vol. 72, No. 10, pp. 1385-1392, Oct. 1982.

Moharam et al., "Rigorous Coupled-Wave Analysis of Planar-Grating Diffraction", Optical Society of America, vol. 71, No. 7, pp. 811-818, Jul. 1981.

Knop, K., "Rigorous Diffraction Theory for Transmission Phase Gratings with Deep Rectangular Grooves", Optical Society of America, vol. 68, No. 9, pp. 1206-1210, Sep. 1978.

Kong, J., "Second-Order Coupled-Mode Equations for Spatially Periodic Media", Optical Society of America, volume 67, No. 6, pp. 825-829, Jun. 1977.

Azzam et al., "Generalized Ellipsometry for Surfaces with Directional Preference: Application to Diffraction Gratings", Journal of the Optical Society of America, vol. 62, No. 12, pp. 1521-1530, Dec. 1972.

Case, S., "Coupled-Wave Theory for Multiply Exposed Thick Holographic Gratings", Optical Society of America, volume 65, No. 6, pp. 724-729, Jun. 1975

Kaspar, F., "Diffraction by Thick, Periodically Stratified Gratings with Complex Dielectric Constant", Journal of Optical Society of America, vol. 63, No. 1, pp. 37-45, Jan. 1973.

Azzam et al., "Application of Generalized Ellipsometry to Anisotropic Crystals", Journal Optical Society of America, volume 64, No. 2, pp. 128-133, Feb. 1974.

Burckhardt, C., "Diffraction of a Plane Wave at a Sinusoidally Stratified Dielectric Grating", Journal of Optical Society of America, vol. 56, No. 11, pp. 1502-1509, Nov. 1966.

Krukar et al., "Reactive Ion Etching Profile and Depth Characterization Using Statistical and Neural Network Analysis of Light Scattering Data", American Institute of Physics, vol. 74, No. 6, pp. 3698-3706, Sep. 15, 1993.

Li, L., "A Modal Analysis of Lamellar Diffraction Gratings in Conical Mountings", Journal of Modern Optics, vol. 40, No. 4, pp. 553-573, year 1993.

Momeni et al., "Pure Coupled Mode Analysis of Diffraction by Isotropic Transmission Volume Gratings", IEEE Transactions on Antennas and Propagation, vol. 52, No. 12, pp. 3304-3311, Dec. 2004.

Momeni et al., "Improved Coupled Wave Analysis of Two-Dimensional Planar Multiple Gratings", IEEE Transactions on Antennas and Propagation, vol. 52, No. 1, pp. 165-171, Jan. 2004.

Garnaes et al., "Profiles of a High-Aspect Radio Grating Determined by Spectroscopic Scatterometry and Atomic-Force Microscopy", Applied Optics, vol. 45, No. 14, pp. 3201-3212, May 10, 2006.

Kallioniemi et al., "Characterization of Diffraction Gratings in a Rigorous Domain with Optical Scatterometry: Hierarchical Neural-Network Model", Applied Optics, vol. 38, No. 28, pp. 5920-5930, Oct. 1, 1999.

Ahmed et al., "Comparison of Beam Propagation Method and Rigorous Coupled-Wave Analysis for Single and Multiplexed Volume Gratings", Applied Optics, vol. 35, No. 22, pp. 4426-4435, Aug. 1, 1996.

Minhas et al., "Ellipsometric Scatterometry for the Metrology of Sub-01-um-linewidth Structures", Applied Optics, vol. 37, No. 22, pp. 5112-5115, Aug. 1, 1998.

Kallioniemi et al., "Optical Scatterometry of Subwavelength Diffraction Gratings: Neural Network Approach", Applied Optics, vol. 37, No. 25, pp. 5830-5835, Sep. 1, 1998.

Huang et al., "Normal-Incidence Spectroscopic Ellipsometry for Critical Dimension Monitoring", Applied Physics Letters, vol. 78, No. 25, pp. 3893-3985, Jun. 18, 2001.

U.S. Appl. No. 12/592,773 Official Action dated Sep. 1, 2010.

* cited by examiner

OPTICAL VACUUM ULTRA-VIOLET WAVELENGTH NANOIMPRINT METROLOGY

CROSS-REFERENCE TO RELATED APPLICATION

This application claims the benefit of U.S. Provisional Patent Application 61/433,526, filed Jan. 18, 2011, which is incorporated herein by reference.

TECHNICAL FIELD OF THE INVENTION

This invention relates to an optical metrology apparatus and method for measuring nanoimprint structures. One aspect of the invention is the use of Vacuum Ultra-Violet (VUV) incident radiation to enhance sensitivity to multiple structural and residual thickness parameters of structures formed during the nanoimprint and subsequent etching processes. Embodiments of the invention advantageously simplify the optical analysis of nanoimprint structures by making use of the fact that typical nanoimprint feature sizes are significantly smaller than typical incident wavelengths. While polarization of the incident light can be beneficial in some cases, one embodiment of the current invention advantageously avoids polarizing the incident light.

BACKGROUND OF THE INVENTION

Nanoimprint lithography is quickly gaining ground as a cost-effective substitute for optical lithography as feature sizes across the electronics industries continue to shrink.

The hard disk drive manufacturing industry is becoming an early adopter of nanoimprint technology. The need to continually increase disk media areal densities has led to the development of Discrete Track Recording (DTR) media and Bit Patterned Media (BPM), typically consisting of concentric lines and grooves in the case of DTR, and 2-dimensional grids of holes in the case of BPM. Roadmap goals for DTR and BPM structures are 20 nm and 25 nm half pitch, respectively, to be achieved in progressive steps between now and 2015 ("From Possible to Practical—The Evolution of Nanoimprint Lithography for Patterned Media", P. Hofemann, Session 6, Diskcon Asia-Pacific (2009)).

Examples of attempts to apply conventional scatterometry and/or optical critical dimension (OCD) solutions to nanoimprint lithography in the prior art focus mainly on larger feature sizes, and ignore—or simply brush off without further comment—the trends of disk media roadmaps that will eventually result in much smaller feature sizes. Examples include "Characterizing Nanoimprint Profile Shape and Polymer Flow Behavior using Visible Light Angular Scatterometry", R. Alassaad, L. Tao, S. W. Pang, and W. Hu, Nano Lett. Vol 6. No. 8, pp. 1723-1728 (2006); "Scatterometry for in situ measurement of pattern reflow in nanoimprinted polymers", H. J. Patrick, T. A. Germer, Y. Ding, H. W. Ro, L. J. Richter, and C. L. Soles, Appl. Phys. Lett, Vol. 93, 233105 (2008); and "Fully Automated Non-Destructive Metrology for Imprint Templates, DTR, and BPM Media", I. Bloomer, Session 7, Diskcon Asia-Pacific (2009).

SUMMARY

As in nearly all aspects of micro/nano-device manufacturing, strict process control via metrology feedback is desirable. Optical metrology exhibits strong advantages over conventional direct imaging techniques, such as scanning electron microscopy (SEM), or mechanical techniques, such as atomic force microscopy (AFM). Optical metrology is typically fast and nondestructive, which is especially advantageous in high volume production environments. A common use of optical metrology is to scan many (or all) parts, with alarm limits set to flag parts that fall outside a desired process range. The flagged parts are then often studied more closely using the direct/mechanical metrologies. The high sampling rate of optical techniques translates to the ability to flag potential problems much earlier than by using direct techniques alone.

Were the DTR and BPM feature sizes at least comparable to the typical wavelengths used for deep ultra-violate to near infra-red (NIR) optical metrology, traditional scatterometry or optical critical dimension (OCD) metrologies might have been viable solutions for process control. However, process control of DTR and BPM nanoimprint processes requires the extraction of multiple geometric parameters in addition to a residual layer thickness. The minimum wavelength of 190-200 nm used by conventional DUV-NIR optical systems is many times the typical nanoimprint feature size, which causes a drastic reduction in multiple parameter sensitivity when using conventional optical metrology. In order to maintain resolution of the metrology, a decrease of the incident wavelength below the DUV region is required.

A second aspect of materials involved in the nanoimprint process is that they are typically transparent in the DUV-NIR wavelength range. These same materials often exhibit strong absorption characteristics in the VUV region, leading to a significant enhancement of optical characterization ability when using VUV metrology. The benefits of probing VUV absorption often equal or even outweigh the benefits of the decreased incident wavelength-versus-feature size achieved when using VUV metrology.

Of the above mentioned prior art, Bloomer (2009) is the only one that addresses the disk industry nanoimprint roadmap, but incorrectly concludes that single-parameter sensitivity simulations are sufficient for establishing the extendibility of the metrology. Conversely, in order to prove that an indirect technique such as an optical metrology is capable of simultaneously extracting multiple parameters from a recorded spectrum, one must take into account the full covariance behavior of the system (see, for example W. H. Press, S. A. Teukolsky, W. T. Vetterling, and B. P. Flannery, *Numerical Recipes in C* ($2^{nd}$ *Edition*), Chapt. 15, Cambridge University Press, Cambridge, 1992; and similar concepts in "Accuracy Limitations in Specular-Mode Optical Topography Extraction", F. L. Terry, Jr., Proceedings of the SPIE, Vol. 5038, pp. 547-558 (2003)). The work of Terry (2003) in particular illustrates how an ability to extract multiple parameters from a relatively large structure does not translate to similar ability when the same structure is scaled down in size. Taking covariance analysis into account, the metrology described in Bloomer (2009) can be readily shown to be non-extendable to nanoimprint roadmap feature sizes. Thus, the prior art does not adequately address the impending reduction of structure feature sizes compared to conventional optical metrology wavelengths.

In order to control multiple processing parameters and still take advantage of the benefits that optical metrology offers, a VUV optical metrology solution for nanoimprint control is desirable. The fundamental resolution limit occurs at smaller feature sizes since the minimum probe wavelength is smaller. As feature sizes shrink to significantly less than even VUV wavelengths, nanoimprint metrology becomes analogous to thin film metrology. In this case VUV absorption continues to offer advantages in terms of decoupling more simultaneous parameters than is possible using conventional DUV-NIR wavelength metrology.

Some embodiments of the present invention provide an optical metrology apparatus for measuring nanoimprint and nanoimprint template structures using VUV-NIR incident radiation. One embodiment utilizes incident radiation polarized in particular directions with respect to the nanoimprint structure. For example, over the area of a typical measurement spot (~30 um diameter), a DTR structure is approximately a 1-D periodic structure (i.e., a grating), and the incident radiation may be polarized so that either the incident electric field is parallel to the DTR lines (TE polarization), or the incident magnetic field is parallel to the DTR lines (TM polarization). Other polarization directions may be equally beneficial. Alternately, another embodiment uses approximately un-polarized incident radiation, and does not need to further align the measured structures to the optical system. Yet another embodiment combines polarized incident light of one wavelength range, for example DUV-NIR, with un-polarized light of VUV wavelengths.

In some embodiments, the rigorous coupled-wave (RCW) method or other suitable rigorous diffraction analysis is used to analyze the recorded optical spectra ("Formulation for stable and efficient implementation of the rigorous coupled-wave analysis of binary gratings", M. G. Moharam, E. B. Grann, D. A. Pommet, and T. K. Gaylord, J. Opt. Soc. Am. A, Vol. 12, No. 5, pp. 1068-1076 (1995)). Nanoimprint structures are distinct from traditional scatterometry targets in that the feature size is typically small compared to metrology incident wavelength. This means that a relatively small number of spatial harmonics are required for accurate calculations using the RCW method, so that it may be advantageously used without the need to develop complicated symmetry reductions or library database systems.

In yet other embodiments, the thin film analogy valid for small pitched gratings can be exploited to make use of thin film processing models, such as the effective medium approximation (EMA). In some cases, a structure with a varying profile shape can be treated as an effective film with a vertical inhomogeneity of its optical properties. Such treatment further simplifies analysis and extraction of structural properties.

The thin film analogy can be further exploited by simplifying the analysis of interactions between the response light from the structures and the optical system. In most cases, such interactions do not need to be fully accounted for, and in many cases can simply be ignored. For example, a high numeric objective can be used with a simplified angle-of-incidence distribution. For a particular type of focusing objective, a single effective angle of incidence can be used in the calculations in place of the full range of incident angles, with negligible effect on the results. Likewise, while latent polarization of the optical system is minimized in a preferred embodiment, the relatively small polarization effect of nanoimprint structures means that the latent polarization need not be eliminated completely.

DESCRIPTION OF THE DRAWINGS

FIG. 8c shows relative weights of various angles of incidence on a grating sample structure corresponding to a focusing objective similar to the one shown in FIG. 10a.

It is noted that the appended drawings illustrate only exemplary embodiments of the invention and are, therefore, not to be considered limiting of its scope, for the invention may admit to other equally effective embodiments.

DETAILED DESCRIPTION OF EMBODIMENTS

In a common implementation of a nanoimprint process, a master template is manufactured using e-beam or similar lithography. The master template is typically made of quartz, fused silica, or nickel. Usually, the master template is used to manufacture many secondary templates using a nanoimprint process. The secondary templates are also quartz or sometimes a flexible polymer. During the nanoimprint step, the substrate is first coated with a polymer resist, which is then imprinted using the template. The resist is allowed to flow into the grooves of the template. Then the resist is cured and the template removed, leaving a resist structure that is the inverse of the template structure. In contrast to optical lithography, the nanoimprint is a one-to-one process, with no feature size reduction.

Normally there is a small amount of residual resist left between the resist features and substrate. This residual layer is usually cleared by etching with a chemistry that attacks the resist but not the substrate, leaving resist lines protecting some areas of the substrate but not others. The substrate can then be etched using standard methods.

Figure 1A:
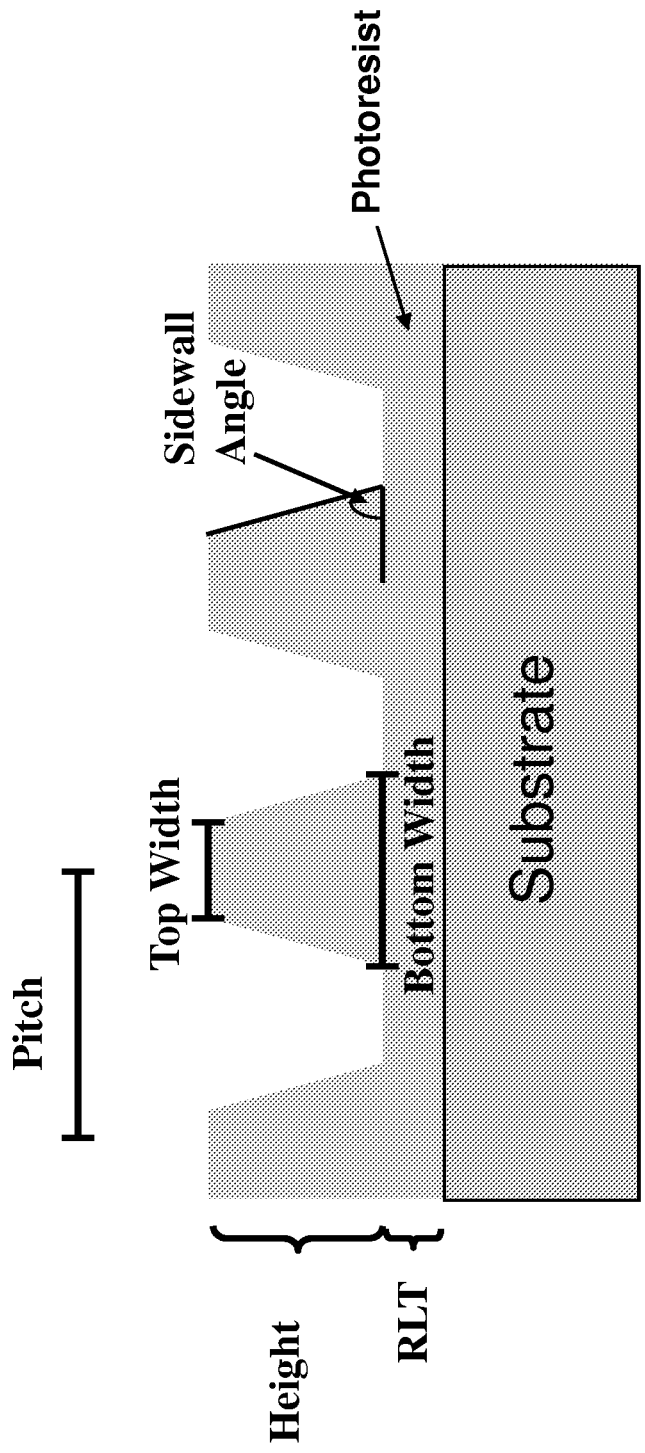
FIG. 1a shows a profile view of a typical nanoimprint structure.
Figure 1B:
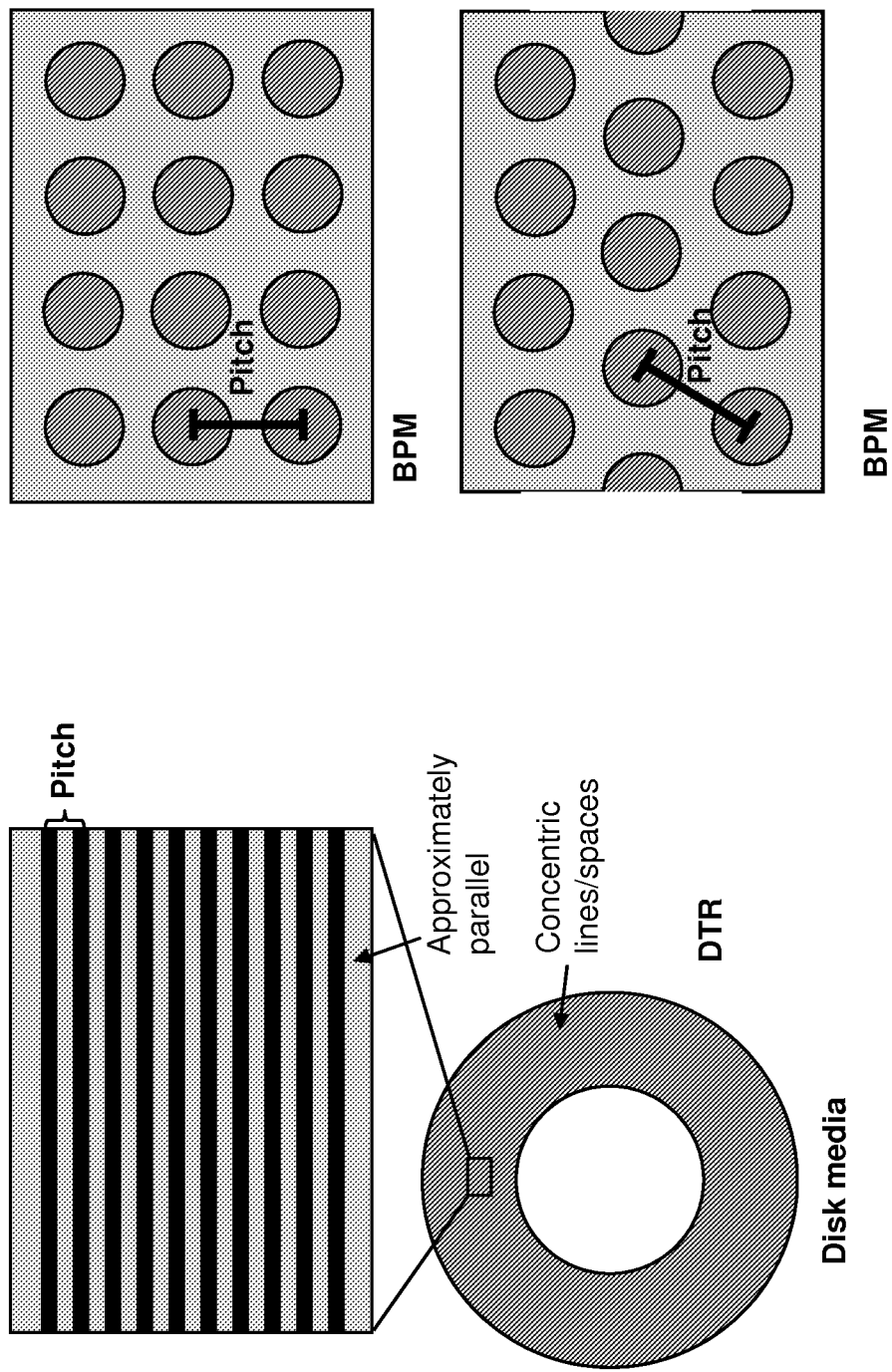
FIG. 1b shows top-down views of DTR and BPM structures.
Figure 2:
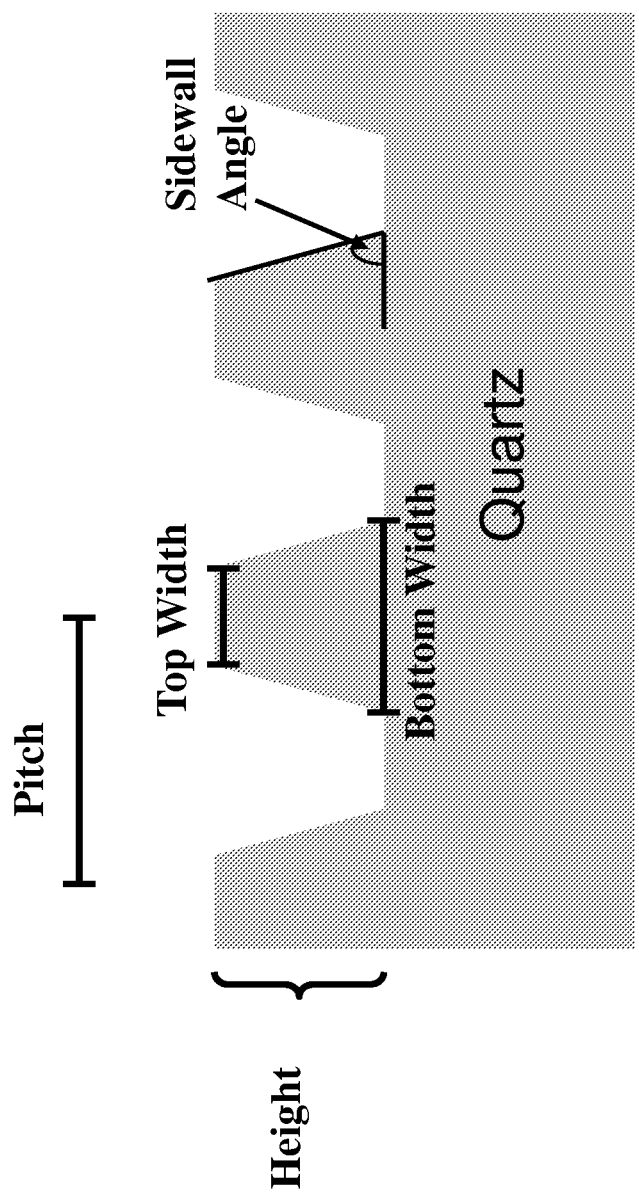
FIG. 2 shows a profile view of a typical nanoimprint template structure.

FIG. 1a illustrates a typical nanoimprinted resist structure. FIG. 1b illustrates the top-down geometry of DTR and BPM structures. FIG. 2 illustrates a quartz template structure. Typical desired process parameters to be measured by a production metrology include the residual layer thickness (RLT), feature height, feature width, and feature sidewall angle in the case of the imprinted resist, and feature height, width, and sidewall angle in the case of the template structure.

Some of the prior art (Alasaad (2006), Patrick (2008), Bloomer (2009)) attempts to implement classical scatterometry and/or OCD methodology to nanoimprint structures. The basic methodology collects either wavelength- or angle-dependent spectra of light reflected, transmitted, and/or polarized by the sample. The measured spectrum (reflectance, transmittance, ellipsometric psi and delta, etc.) is usually not very enlightening by itself, but indirectly contains information about the structure being measured. This information can be extracted by fitting the data to a mathematical model of the assumed structure using a regression analysis (see, for example, the Levenberg-Marquardt routine in Chapter 15 of Press (1992)), whereby the parameters describing the structure such as film thickness, width, sidewall angle, etc. are optimized, and the ones most likely to have resulted in the measured spectra determined.

The Levenberg-Marquardt regression optimizes the model parameters by minimizing a figure of merit called the chi-squared function, defined by $$\chi^2 = \sum_{i=1}^{N} \left[ \frac{y_i - y(x_i; a)}{\sigma_i} \right]^2, \quad \text{Eq. 1}$$

where $x_i$ are the independent parameter (usually incident wavelength, angle, and sometimes polarization), $y_i$ are the measured data at incident condition $x_i$, $a=(a_1, a_2, \ldots, a_m)$ is a set of m values of the model parameters, $y(x_i;a)$ is the model calculation for incident condition $x_i$ and parameter set a, and $\sigma_i$ is the standard deviation of the measured data about the mean value—i.e., the uncertainty in the measured value of $y_i$. Simply put, the Levenberg-Marquardt algorithm is a method of testing different values of a until the smallest chi-squared value is found, within the limits of statistical significance. By inference, the resulting optimal parameter set, $a_{min}$, is the most likely cause of the measured data.

The chi-squared function can be viewed as topography over an m-dimensioned parameter space, with "valleys" in regions of smaller chi-squared values and "hills" in regions of larger chi-squared values. The goal of the fit procedure is to find the lowest value of the chi-squared function. The Levenberg-Marquardt routine is very efficient at finding the lowest local point, inside the starting valley. Since the multi-dimensional chi-squared topography can be very complicated, with many local minima, the Levenberg-Marquardt routine is sometimes combined with course grid search methods designed to find the correct starting valley. The regression then efficiently finds the local minimum, which is now the global minimum, assuming the correct starting region was found.

A problem with the conventional scatterometry/OCD approach is that nanoimprint feature sizes are very small compared to the incident wavelength, which typically lies in the DUV-NIR wavelength range. This results in massive ambiguity of the measured data—i.e., multiple sets of structural parameters result in nearly identical spectra. Another way to state this is that the chi-squared function in Eq. 1 has multiple, very similar global minimum values. The only way to alleviate this problem for a given metrology configuration is to reduce the number of parameters in the parameter set a. This approach reduces the number of parameters that can be measured using the metrology.

A dramatic example is given in Terry (2003), where a 230-825 nm spectroscopic ellipsometer is used to extract many profile parameters for a resist structure with ~350 nm wide resist lines in a 700 nm pitch grating. The result is a fairly detailed reproduction of the shape of the actual resist profile structure. A simulated structure was scaled down to ~40 nm wide lines in a 90 nm pitch grating, but with the same overall profile shape as the 700 nm pitch structure. This simulated structure was refit using a simple rectangular model. Differences in the simulated and refit data were well within the random and systematic noise limits of the ellipsometer, which had clearly lost the ability to extract detailed profile shape information. This loss of ability is entirely due to the shrinking feature size versus incident wavelength. The type of optical metrology is only partly relevant—the same argument could have been equally well applied to polarized or unpolarized reflectance data.

The main impact of shrinking nanoimprint feature sizes on optical metrology is the loss of sidewall control for both nanoimprint and template structures. The loss of sidewall control is not due to a loss of sensitivity to changes in sidewall parameter. FIGS. 3a-3c in the above-mentioned provisional patent application illustrate sensitivity of DUV-NIR wavelength polarized reflectance and polarized transmittance measurements of a quartz template structure with nominal parameters 80 nm pitch, 40 nm depth, 36.5 nm top width, and 43 nm bottom width. Note that the sidewall angle can be calculated from the height, top width, and bottom width, and is 85.35° for this structure. FIG. 3a shows sensitivity to 2 nm changes in feature height, FIG. 3b shows sensitivity to 2 nm changes in top width, and FIG. 3c shows sensitivity to bottom width. Individual sensitivity to all three parameters, and therefore to sidewall angle, is evident, and furthermore the reflectance and transmittance changes occur throughout the DUV-NIR wavelength region. FIGS. 4a-4d in the provisional patent application illustrate why this apparent sensitivity does not result in real sidewall measurement capability. FIG. 4a shows changes in TE polarized reflectance for four distinct structures, each having a very different sidewall angle. FIGS. 4b, 4c, and 4d show TM polarized reflectance, TE polarized transmittance, and TM polarized transmittance, respectively, for the same four structures. The maximum reflectance and/or transmittance change is less than 0.05% (absolute scale). Such small differences are very hard to detect, especially in light of systematic errors and uncertainties that affect reflectance and transmittance measurements.

Smaller, but still significant parameter differences result in parameter sets even less distinct in their measured spectra. There are in fact an infinite number of parameter sets, with values lying between those shown in FIG. 4 of the provisional application, that are for all practical purposes indistinguishable to the metrology. Alternately, shrinking the pitch and/or height even further from these nominal results in even more ambiguity, with ever larger parameter differences becoming indistinguishable to the metrology. Thus, the loss of resolution as feature size decreases manifests as reduced ability to simultaneously determine changes in multiple parameters, and can happen even when the probe spectra shows basic sensitivity to changes in individual parameter values.

Covariance analysis can be used to systematically study the underlying uncertainty of a given system (Press (1992), Chapter 15). The covariance matrix is related to the curvature matrix:

$$\alpha_{jk} = \sum_{i=1}^{N} \frac{1}{\sigma_i^2} \left[ \frac{\partial y(x_i; a)}{\partial a_j} \frac{\partial y(x_i; a)}{\partial a_k} \right]_{a=a_{min}}, \quad \text{Eq. 2}$$

which is the second derivative matrix of the chi-squared topography. The covariance matrix is related to the curvature matrix by $$C = \alpha^{-1}. \quad \text{Eq. 3}$$

Under ideal conditions, where the errors in the $y_i$ are perfectly random and there are no strong correlations between the various parameters in a, the 1-sigma standard uncertainties for the individual parameters can be predicted from the diagonal elements of the covariance matrix:

$$\sigma_j = \sqrt{C_{jj}} \quad \text{Eq. 4}$$

For practical reflectance or transmittance measurements, the condition of random uncertainty in the $y_i$ is usually approximately met for short-duration static precision runs. If the wavelength dependence of $\sigma_i$ in Eq. 2 is correctly taken into account, Eq. 4 is a pretty good predictor of short-term static precision. Even when the random noise and correlation assumptions are not strictly met, the covariance analysis can still give a relative comparison between different technologies, or between different wavelength ranges of similar technologies.

The elements of the curvature matrix affect the predicted uncertainties in two ways, the first being basic sensitivity via the diagonal terms in Eq. 2. The second is correlation between multiple parameters. A measure of the degree of correlation between two parameters is contained in the off-diagonal covariance elements:

$$r_{ij} = \frac{C_{ij}}{\sqrt{C_{ii} C_{jj}}}, \quad \text{Eq. 5}$$

where $r_{ij}$ is the cross-correlation factor for parameters i and j. A value near ±1 indicates a highly correlated pair of parameters, with 1 indicating positive correlation, and −1 indicating inverse correlation. The cross-correlation factors do not indicate the effects, if any, of three or more parameter correlations.

It should be pointed out that the static precision of an instrument represents only its best case theoretical performance. Real-world performance involves loading and unloading samples, moving sample holders, calibrating the system using reference samples with assumed reflectance values, moving polarizers, etc. All of this contributes to significant systematic error. Unlike perfectly random error, systematic error can change the wavelength-dependent shape of measured spectra. Generally speaking, reflectance and transmittance measurements should be viewed as no more accurate than ~0.1% absolute, even under the best of conditions. The practical result is that strong parameter correlations must be taken seriously even if the associated 1-sigma precision values appear reasonable. Small deviations in the spectra during dynamic repeatability and long-term stability runs will likely result in instability of the highly-correlated parameters.

The results shown in the above-mentioned provisional application could have been predicted by simply calculating the covariance matrix for the nominal structure of FIG. 3a. The result is shown in Table 1.

TABLE 1

Covariance matrix (top) and extracted uncertainties and cross-correlation factors (bottom) for simultaneous TE and TM polarized R and T (4 spectra total) of a quartz template structure having nominal parameters 40 nm height, 36.5 nm top width, and

|  | Height | Bottom Width | Top Width |
|---|---|---|---|
| Height | 0.5573 | 1.6567 | −1.6077 |
| Bottom Width | 1.6567 | 4.9639 | −4.7816 |
| Top Width | −1.6077 | −4.7816 | 4.6553 |

| 1-σ height (nm) | 1-σ Bottom Width (nm) | 1-σ Top Width (nm) | Cross-correlation: height-bottom width | Cross-correlation: height-top width | Cross-correlation: bottom width-top width |
|---|---|---|---|---|---|
| 0.747 | 2.23 | 2.16 | 0.996 | −0.998 | −0.995 |

Figure 4:
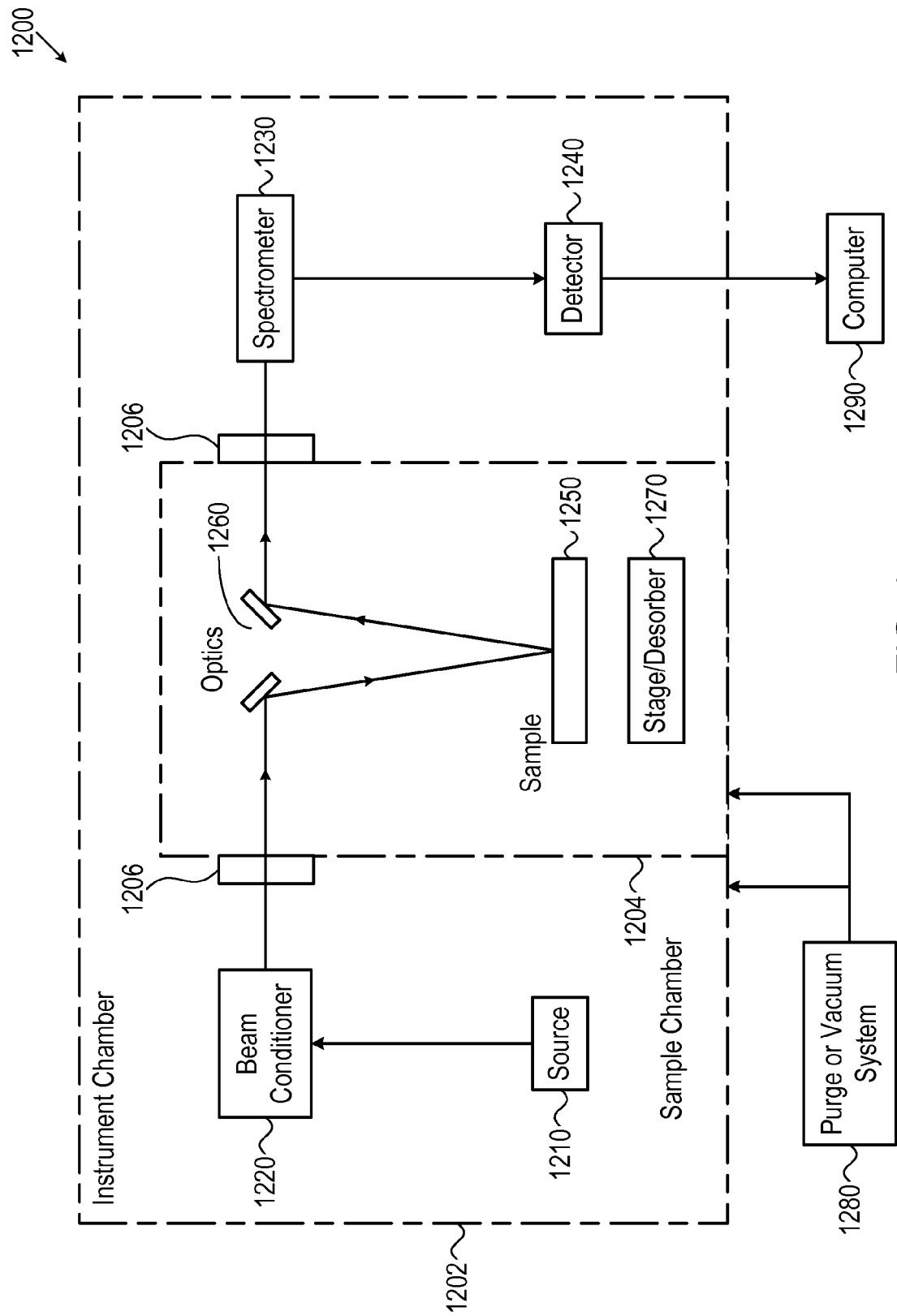
FIG. 4 is a schematic representation of a reflectometer.

The cross-correlation factors are all close to 1 or −1, indicating highly correlated parameters. In this context, the various structures in FIG. 4 of the provisional application leading to similar spectra are different combinations of the measured parameters that "trade" values amongst themselves in a manner consistent with the covariance result: the nominal structure can be replaced by one with larger height and appropriately larger bottom width (positive correlation) and smaller top width (negative correlation), etc. Basically, FIG. 4 shows the practical interpretation of the covariance result given in Table 1.

Since the loss of multiple parameter capability is a direct consequence of loss of resolution due to shrinking feature size versus probe wavelength, a way to increase sensitivity to multiple parameters is to decrease the incident wavelength. Table 2 gives the covariance analysis result for the template example presented in FIG. 3 of the above-mentioned provisional application for one embodiment of the present invention, configured for 120-800 nm (VUV-NIR) un-polarized reflectance.

TABLE 2

Covariance matrix (top) and extracted uncertainties and cross-correlation factors (bottom) for VUV-NIR un-polarized reflectance of a quartz template structure having nominal parameters 40 nm height, 36.5 nm top width, and 43 nm bottom width.

|  | Height | Bottom Width | Top Width |
|---|---|---|---|
| Height | 0.0122 | 0.0004 | −0.0215 |
| Bottom Width | 0.0004 | 0.1583 | 0.0610 |
| Top Width | −0.0215 | 0.0610 | 0.0737 |

TABLE 2-continued

Covariance matrix (top) and extracted uncertainties
and cross-correlation factors (bottom) for VUV-NIR
un-polarized reflectance of a quartz template structure
having nominal parameters 40 nm height,
36.5 nm top width, and 43 nm bottom width.

| 1-σ height (nm) | 1-σ Bottom Width (nm) | 1-σ Top Width (nm) | Cross-correlation: height-bottom width | Cross-correlation: height-to width | Cross-correlation: bottom width-top width |
|---|---|---|---|---|---|
| 0.111 | 0.398 | 0.272 | 0.010 | −0.718 | 0.565 |

Figure 3:
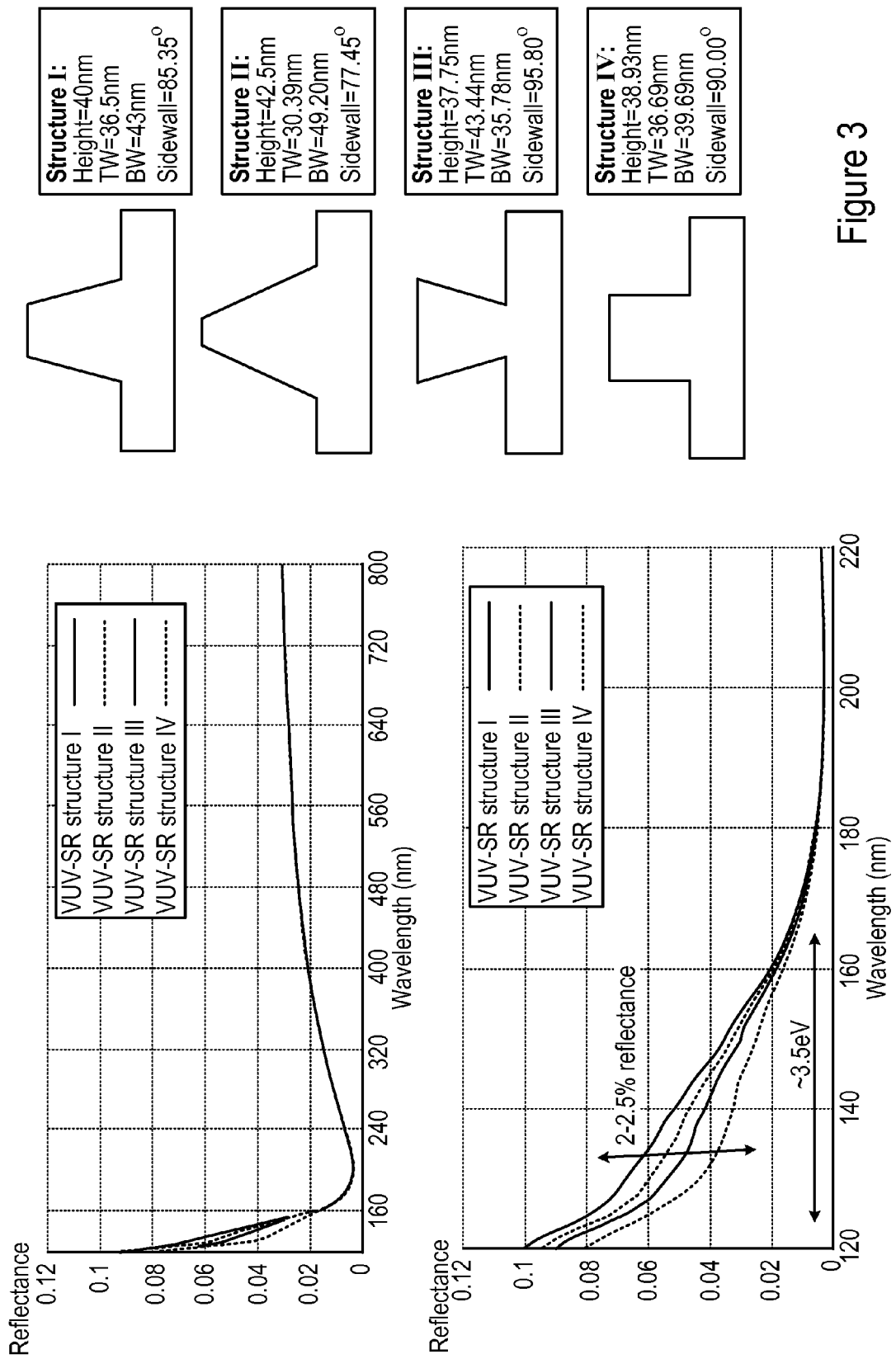
FIG. 3 shows sensitivity to four distinct template structures for an embodiment of the present invention.

The covariance results in Table 2 show better sensitivity to individual parameters, but more importantly, none of the cross-correlation terms are close to 1 or −1. This means that embodiments of the present invention are sensitive to changes in combinations of template parameters that the conventional DUV-NIR scatterometry is not. This fact is illustrated in FIG. 3 of the present patent application, which shows 120-800 nm un-polarized reflectance for the four template structures shown in FIG. 4 of the provisional application. Not only can the present embodiments easily distinguish the different structures, but FIG. 3 makes it clear that the VUV region is critical for achieving this sensitivity.

However, decreasing the metrology wavelength below that used by conventional scatterometer systems implies moving into the vacuum ultra-violet wavelength regime, and is not trivial. In particular, VUV light is absorbed by moisture and oxygen, and so either the ambient around the sample and optics must be evacuated and replaced by an inert gas, or a continuous flow of inert gas must be used to purge the environment around the measurement area. Furthermore, calibration samples and optical components are susceptible to contamination caused by airborne molecular contamination (AMC) as well as contamination from out-gassing materials, and special calibration and cleaning techniques must be employed.

Embodiments of the present invention provide a method for applying VUV reflectance measurements to nanoimprint metrology, a preferred embodiment of which incorporates a VUV reflectometer apparatus and method known in the prior art, via U.S. Pat. Nos. 7,026,626, 7,067,818, 7,126,131, 7,282,703, 7,342,235, and 7,511,265, all incorporated herein by reference. While some resolution enhancement is achieved via reduced wavelength versus feature size, the enhanced metrology capabilities are due more to the distinct VUV absorption exhibited by most nanoimprint and template materials. Thus, some embodiments of the present invention provide enhanced sensitivity over DUV-NIR systems even when feature sizes have shrunk beyond resolution limits of VUV wavelengths.

A schematic representation of an optical reflectometer metrology tool 1200 that depicts one technique disclosed herein is presented in FIG. 4 of the present patent application. As is evident, the source 1210, beam conditioning module 1220, optics (not shown), spectrometer 1230, and detector 1240 are contained within an environmentally controlled instrument (or optics) chamber 1202. The sample 1250, additional optics 1260, motorized stage/sample chuck 1270 (with optional integrated desorber capabilities), and sample are housed in a separate environmentally controlled sample chamber 1204 so as to enable the loading and unloading of samples without contaminating the quality of the instrument chamber environment. The instrument and sample chambers are connected via a controllable coupling mechanism 1206 which can permit the transfer of photons, and, if so desired, permit the exchange of gases to occur. A purge and/or vacuum system 1280 may be coupled to the instrument chamber 1202 and the sample chamber 1204 such that environmental control may be exercised in each chamber.

Additionally a computer 1290 located outside the controlled environment may be used to analyze the measured data. A computer program for extracting structural and optical parameters from a theoretical model of the nanoimprint structure is included in the computer 1290. The structural properties may be analyzed using rigorous methods such as RCW, or approximate methods that treat the structure as a thin film can be used. It will be recognized that computer 1290 may be any of a wide variety of computing or processing means that may provide suitable data processing and/or storage of the data collected.

While not explicitly shown in FIG. 4, it is noted that the system could also be equipped with a robot and other associated mechanized components to aid in the loading and unloading of samples in an automated fashion, thereby further increasing measurement throughput. Further, as is known in the art load lock chambers may also be utilized in conjunction with the sample chamber to improve environmental control and increase the system throughput for inter-changing samples.

During operation, light from the source 1210 is modified, by way of beam conditioning module 1220, and directed via delivery optics through the coupling mechanism windows 1206 and into the sample chamber 1204, where it is focused onto the sample by focusing optics 1260. Light reflected from the sample is collected by the focusing optics 1260 and re-directed out through the coupling mechanism 1206, where it is dispersed by the spectrometer 1230 and recorded by a detector 1240. The entire optical path of the device is maintained within controlled environments, which function to remove absorbing species and permit transmission of below DUV photons.

Referring again to FIG. 4, the beam conditioner module 1220 allows for the introduction of spatial and/or spectral filtering elements to modify the properties of the source beam. While this functionality may not generally be required, there may arise specific applications where it is deemed advantageous. Examples could include modifying the spatial or temporal coherence of the source beam through use of an aperture, or introduction of a "solar blind" filter to prevent longer wavelength light from generating spurious below DUV signals through scattering mechanisms that may occur at the various optical surfaces in the optical beam path.

The beam conditioner can also include a polarizer, which would be useful for critical dimension measurements where it is desirable to polarize the incident light in a particular direction with respect to the measured structures. Alternately, it may be desirable to have a non-polarizing optical path, and the beam conditioner can consist of a depolarizer to counter the effects of any polarization imparted by the preceding optics. Additionally, either a polarizing or depolarizing beam conditioner can be placed in the optical path on the detection side of the sample. A depolarizer at this location would be useful for eliminating any polarization effects of the detection system.

Figure 5:
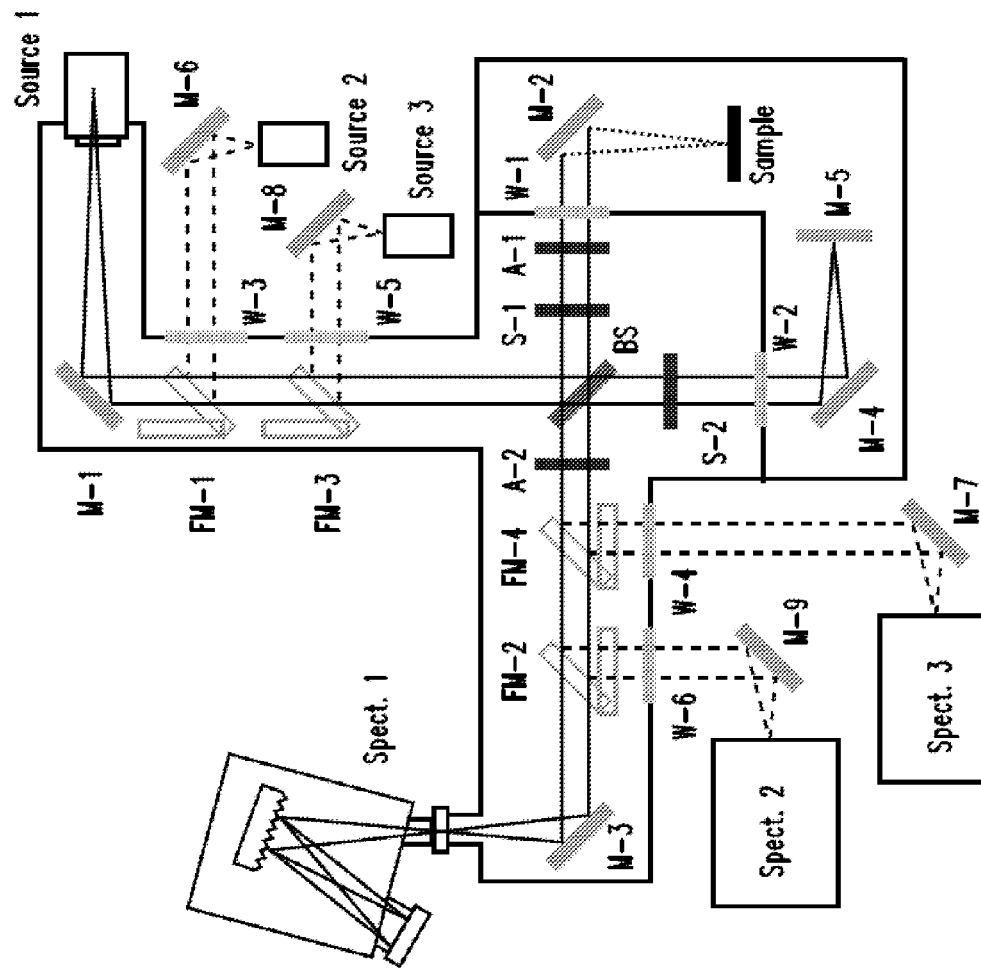
FIG. 5 is a more detailed schematic representation of a reflectometer.

A more detailed schematic of the optical aspects of one embodiment of the instrument is presented in FIG. 5. The instrument is configured to collect referenced broad band reflectance data in the below DUV and two additional spectral regions. During operation, light from these three spectral regions may be obtained in either a parallel or serial manner. When operated in a serial fashion, reflectance data from the below DUV is first obtained and referenced, following which, reflectance data from the second and then third regions is collected and referenced. Once all three data sets are recorded they are spliced together to form a single broad band spectrum. In parallel operation, reflectance data from all three regions are collected, referenced and recorded simultaneously prior to data splicing.

The instrument is separated into two environmentally controlled chambers: the instrument chamber and the sample chamber. The instrument chamber houses most of the system optics and is not exposed to the atmosphere on a regular basis. The sample chamber houses the sample and reference optics, and is opened regularly to facilitate changing samples. Flip-in mirrors FM-1 and FM-3 may be utilized to selectively choose which light source—Source 1, Source 2, or Source 3 is utilized (each having a different spectral region). Flip-in mirrors FM-2 and FM-4 may be utilized to selectively choose one of spectrometers—Spect. 1, Spect. 2, or Spect. 3 (again depending upon the chosen spectral region). As mentioned above with reference to FIG. 4, the spectrometers may be any of a wide variety of types of spectrometers. Mirrors M-6, M-7, M-8 and M-9 may be utilized to help direct the light beams as shown. Windows W-1 and W-2 couple light between the instrument chamber and sample chamber. Windows W-3, W-4, W-5 and W-6 couple light into and out of the instrument chamber. Beam splitter BS and shutters S-1 and S-2 are utilized to selectively direct light to a sample or a reference M-5 with the assistance of mirrors M-2 and M-4 as shown (the reference may be a mirror in one embodiment).

When operated in a serial fashion, below DUV data is first obtained by switching the second spectral region flip-in source mirror FM-1 and third spectral region flip-in source mirror FM-2 into the "out" position so as to allow light from the below DUV source to be collected, collimated and redirected towards beam splitter element BS by the focusing mirror M-1. Light striking the beam splitter is divided into two components, the sample beam and the reference beam, using a near-balanced Michelson interferometer arrangement. The sample beam is reflected from the beam splitter BS and travels through the sample shutter S-1 and sample window W-1 into the sample chamber, where it is redirected and focused onto the sample via a focusing mirror M-2. The reference shutter S-2 is closed during this time. The sample window W-1 is constructed of a material that is sufficiently transparent to below DUV wavelengths so as to maintain high optical throughput.

Light reflected from the sample is collected, collimated, and redirected by the sample mirror M-2 back through the sample window, where it passes through the sample shutter. The light then continues on unhampered by the first spectral region flip-in detector mirror FM-2 and the second spectral region flip-in detector mirror FM-4 (switched to the "out" position), where it is redirected and focused onto the entrance slit of the below DUV spectrometer, Spect. 1, by the focusing mirror M-3. At this point, light from the sample beam is dispersed by the VUV spectrometer and recorded by its associated detector. The spectrometer may be any of a wide variety of spectrometers, including those types disclosed in U.S. Pat. Nos. 7,485,869, 7,579,601, and 7,684,037, the disclosures of which are incorporated herein by reference. Thus, the spectrometer configuration is not intended to be limited to the particular configuration shown in the figure.

Following collection of the sample beam, the reference beam is measured. This is accomplished by closing the sample shutter S-1 and opening the reference shutter S-2. This enables the reference beam to travel through the beam splitter BS, reference shutter S-2, and reference window W-2 into the sample chamber, wherein it is redirected and focused by mirror M-4 onto the plane reference mirror M-5, which serves as the reference surface. It is noted that focusing mirror M-4 may also be a plane mirror such that the reference beam remains collimated as it strikes plane reference mirror M-5. The reference window is also constructed of a material that is sufficiently transparent to VUV wavelengths so as to maintain high optical throughput.

Light reflected from the surface of the plane reference mirror M-5 travels back towards the focusing reference mirror M-4 where it is collected, collimated, and redirected through the reference window W-2 and the reference shutter S-2 towards the beam splitter BS. Light is then reflected by the beam splitter towards the focusing mirror M-3, where it is redirected and focused onto the entrance slit of the VUV spectrometer, Spect. 1. The path length of the reference beam is specifically designed so as to match that of the sample beam in each of the environmentally controlled chambers. To further this end, an optional compensator plate can be inserted between the beam splitter and sample optic M-2 to compensate for the path difference of sample and reference arm due to the beam splitter. Such a compensator plate would consist of the same material as the bulk beam splitter, but without the beam splitter films on the plate surface.

Following measurement of the below DUV data set, the second spectral region data set is obtained in a similar manner During collection of the second region spectral data, both the second spectral region source flip-in mirror FM-1 and the second spectral region detector flip-in mirror FM-2 are switched to the "in" position. As a result, light from the below DUV source, Source 1, is blocked and light from the second spectral region source, Source 2, is allowed to pass through window W-3 after it is collected, collimated, and redirected by its focusing mirror M-6. Similarly, switching the second spectral region detector flip-in mirror FM-2 into the "in" position directs light from the sample beam (when the sample shutter is open and the reference shutter is closed) and reference beam (when the reference shutter is open and the sample shutter is closed) through the associated window W-6 and onto the mirror M-9, which focuses the light onto the entrance slit of the second spectral region spectrometer, Spect. 2, where it is dispersed and collected by its detector.

Data from the third spectral region is collected in a similar fashion by flipping "in" the third spectral region source flip-in mirror FM-3 and the third spectral region detector flip-in mirror FM-4, while flipping "out" the second spectral region source flip-in mirror FM-1 and the second spectral region detector flip-in mirror FM-2.

Once the sample and reference measurements for each of the spectral regions have been performed, a computer or processor (not shown in this figure) can be used to calculate the referenced reflectance spectra in each of the three regions. Finally, these individual reflectance spectra are combined to generate a single reflectance spectrum encompassing the three spectral regions.

When operated in a parallel mode, the source and detector flip-in mirrors are replaced with appropriate beam splitters so that data from all three spectral regions are recorded simultaneously.

Again, a polarizer can be included in the incident optical path before the beam splitter in order to polarize the incident light in a particular direction with respect to the measured structures. Alternately, it may be desirable to have a non-polarizing optical path, and a non-polarizing beam splitter can be used in conjunction with an un-polarized source. If necessary, a depolarizer can be included in the optical path just before the beam splitter to counter the effects of any polarization imparted by the preceding optics. Additionally, either a polarizing or depolarizing beam conditioner can be placed in the optical path on the detection side of the sample, after the beam splitter. A depolarizer at this location would be useful for eliminating any polarization effects of the detection system. However, as will be described, some embodiments of the present invention simply ignore the latent polarization of the optical system, if the polarization properties of the sample allow it. Still other embodiments remove the effects of latent polarization by aligning the sample in a constant fashion with respect to the optics plane. Still other embodiments employ a characterization procedure with a known polarizing sample, in order to calibrate the effects of latent polarization.

When a sample is present, the detected intensity depends on sample properties as well as interactions with optical components throughout the system. In some embodiments, a calibration reference sample of known reflectance is measured just prior to sample measurement, from which effects of the optical system can be calibrated out, resulting in a measurement of the sample reflectance. An additional difficulty in using below DUV spectrometry is caused by a contaminant buildup that occurs on optical components and reference samples due to the interaction of common fab materials/contaminants with high energy radiation. This contaminant buildup has particular relevance to absolute reflectance calibration, since it is difficult to maintain a consistent reference sample. Accordingly, one technique disclosed herein incorporates new calibration procedures as described in U.S. Pat. Nos. 7,282,703, 7,511,265, 7,663,097, and 7,804,059, all of which are incorporated herein by reference. Embodiments of the present invention may also incorporate contaminant monitoring and cleaning techniques as described in U.S. Pat. Nos. 7,342,235, 7,622,310, and 7,663,747, all of which are incorporated herein by reference.

In some embodiments of the present invention, the measured spectra are analyzed using rigorous expansion methods, approximate thin-film methods, or some combination thereof. The reduced feature size versus incident wavelength has a simplifying effect on rigorous expansion methods. For example, the number of expansion orders required for convergence using the RCW method is very small compared to similar, but larger structures. Physically, this is a result of the structure becoming more like a uniform film with respect to the probing optical system. In fact, according to the classical grating equation, small pitch nanoimprint structures do not exhibit long-range diffraction, but reflect only the 0-order specularly reflected light, just as in the case of a uniform or bi-axial thin film. Thus the problem of measuring structural information becomes analogous to a thin film thickness and optical dispersion extraction (see Terry 2003). Many nanoimprint applications can be treated as such, and rigorous grating methods done away with altogether. Effective medium approximations (EMA) specifically designed for measuring small pitch structures can be employed (for example, "On the effective medium theory of subwavelength periodic structures", P. Lalanne and D. L. Lalanne, J. Mod. Opt, Vol. 43, No. 10, pp. 2063-2085 (1996)). However, the thin film analogy can be taken even further by measuring un-polarized reflectance and analyzing it with a basic thin film effective medium theory such as the Bruggeman effective medium theory (D. E. Aspnes in *Handbook of Optical Constants of Solids*, Vol. 1, edited by E. D. Palik, Academic Press, 1998, p. 105). In many cases, such a theory can be used without further consideration, and in many more cases can be used for process monitoring at the expense of a constant offset. For a given nominal structure, an approximate model can be tested against simulations using exact rigorous models to verify that the approximate model can correctly determine changes in structural parameters, and to determine the offset required, if any, in order to render the approximate model accurate.

An embodiment of the present invention alternatively utilizes rigorous or effective thin film models, as appropriate. The analysis method used will typically depend on the nominal structure to be measured, and can be included as part of the analysis recipe for that type of structure. For example, a ~70 nm pitch imprinted resist structure would use an effective medium analysis, while a ~120 nm pitch fused silica template structure might use an RCW analysis. The selection of analysis method is set automatically, along with measurement locations, when the metrology tool operator selects the measurement recipe for either the 70 nm imprinted resist or 120 nm template. In both cases, the analysis is advantageously simplified since the pitch is small compared to the incident wavelength.

The RCW method is described in detail in Moharam (1995). The RCW method expands the field components inside and outside the grating region in terms of generalized Fourier series. The method consists of two major parts—an eigen-problem to determine a general solution inside the grating layer, and a boundary problem to determine the reflected and transmitted diffracted amplitudes along with the specific solution for the fields inside the grating region. The Fourier series are truncated after a finite number of terms. The truncation is usually characterized by the truncation order, N, which means that 2N+1 spatial harmonics are retained in the series (positive and negative terms up to ±N, and the 0 term). The truncation order N is determined by the convergence properties of the diffraction problem, and is usually chosen as the smallest value of N such that increasing the value of N would have a negligible effect on the calculated spectra. The number of orders required for convergence of the spectra is strongly structure dependent. In general, more orders are required for larger pitch-to-wavelength ratios, and more orders are required for metallic structures than for dielectric structures.

The number of orders required for convergence critically affects calculation speed, which scales as order $N^3$. Typical data collection times are less than 10 seconds for some embodiments of the present invention, making data collection very fast compared to conventional metrologies. However, since a regression analysis of the spectrum is required in order to extract useful process parameters, it is desirable to have an analysis time comparable to or faster than the data collection time. The analysis time can easily be dominated by the theoretical spectrum calculation, which typically must be done many times per regression. Therefore, the truncation order N is a primary factor in determining whether the analysis step is likely to bottle-neck the measurement. For low truncation orders, the RCW calculation can typically be implemented in a straight-forward manner on typical desktop workstations without causing bottleneck. For higher required orders, the calculation speed is reduced, and additional procedures may need to be employed, such as parallel implementation of the spectrum calculation. In extreme cases, a real-time regression may not be feasible, and a scatterometry library consisting of all possible calculated spectra (within process limits and parameter grid size) is generated, and then searched to find the best-fit spectrum during the actual measurement.

In addition to the field components, the RCW method also represents the grating region permittivity as a Fourier series. For a binary periodic structure with refractive indices of $n_{rd}$ for the lines and $n_{gr}$ for spaces, the Fourier expansion of the grating permittivity is $$\sum_h \varepsilon_h \exp\left(j\frac{2\pi h x}{\Lambda}\right),\quad \text{Eq. 6}$$

where $$\varepsilon_0 = n_{rd}^2 f + n_{gr}^2(1-f),$$

$$\varepsilon_h = (n_{rd}^2 - n_{gr}^2)\frac{\sin(\pi h f)}{\pi h},$$

x is the direction of the periodicity, and f is the filling factor, which is the fraction of the structure made up of lines with index $n_{rd}$. For a truncation order of N, the RCW method incorporates permittivity Fourier terms up to ±2N into the coupled equations. The permittivity written out explicitly for a truncation order of 0 is simply $$\varepsilon(x) = n_{rd}^2 f + n_{gr}^2(1-f),\quad \text{Eq. 7}$$

which is independent of x. Basically, if the calculated spectrum for a particular structure has converged with a truncation order of 0, the RCW method treats the structure as a uniform film with a permittivity that is the geometric average of the line and space permittivities. Since the order required for convergence depends on the incident metrology wavelength as well as the structure, Eq. 7 implies that the metrology is insensitive to the fact that there is any lateral structure at all, and only senses the structure through an average effect on the area covered by the grating structure. In this case, the diffraction problem is equivalent to determining the thickness and refractive index of a uniform film. Since the effective refractive index depends on the line/space filling factor f, the average CD can still be determined from a thickness and refractive index measurement as long as the grating pitch is known. However, the structure cannot be distinguished from a uniform film that has the same effective refractive index.

For a structure where convergence is reached with a truncation order of 1, the grating permittivity does depend on x:

$$\varepsilon(x) = n_{rd}^2 f + n_{gr}^2(1-f) + 2(n_{rd}^2 - n_{gr}^2)\frac{\sin(\pi f)}{\pi}\cos(2\pi x/\Lambda) + \quad \text{Eq. 8}$$
$$2(n_{rd}^2 - n_{gr}^2)\frac{\sin(2\pi f)}{2\pi}\cos(4\pi x/\Lambda).$$

Even though Eq. 8 does not represent the full rectangular-shaped line/space structure, the RCW method does treat this structure as being distinct from a uniform film. For structures that are very small compared to the incident metrology wavelength, it is possible to get an idea of the degree to which it is necessary to take into account the lateral variation of the structure by comparing the N=0 and N=1 spectra.

Figure 6A:
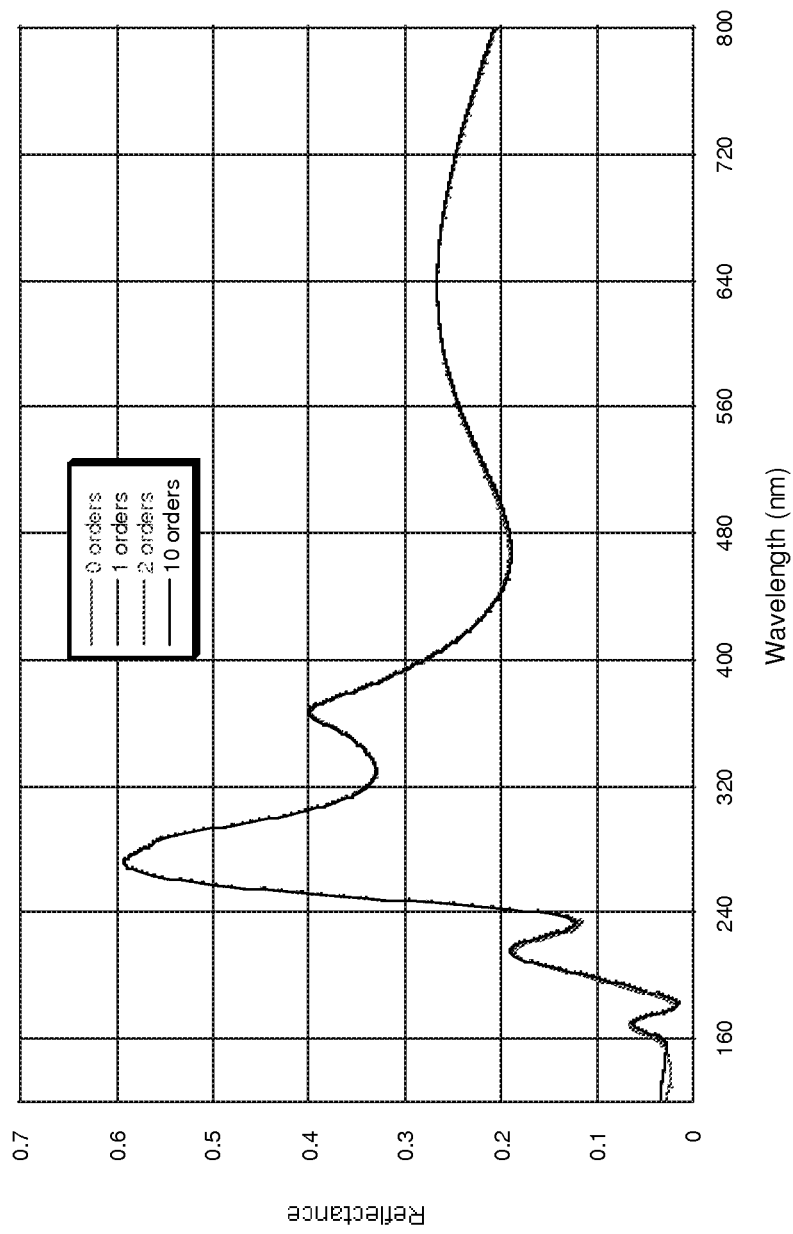
FIG. 6a shows a convergence simulation for a 64 nm pitch, 32 nm width, 77 nm height imprinted resist structure.
Figure 6B:
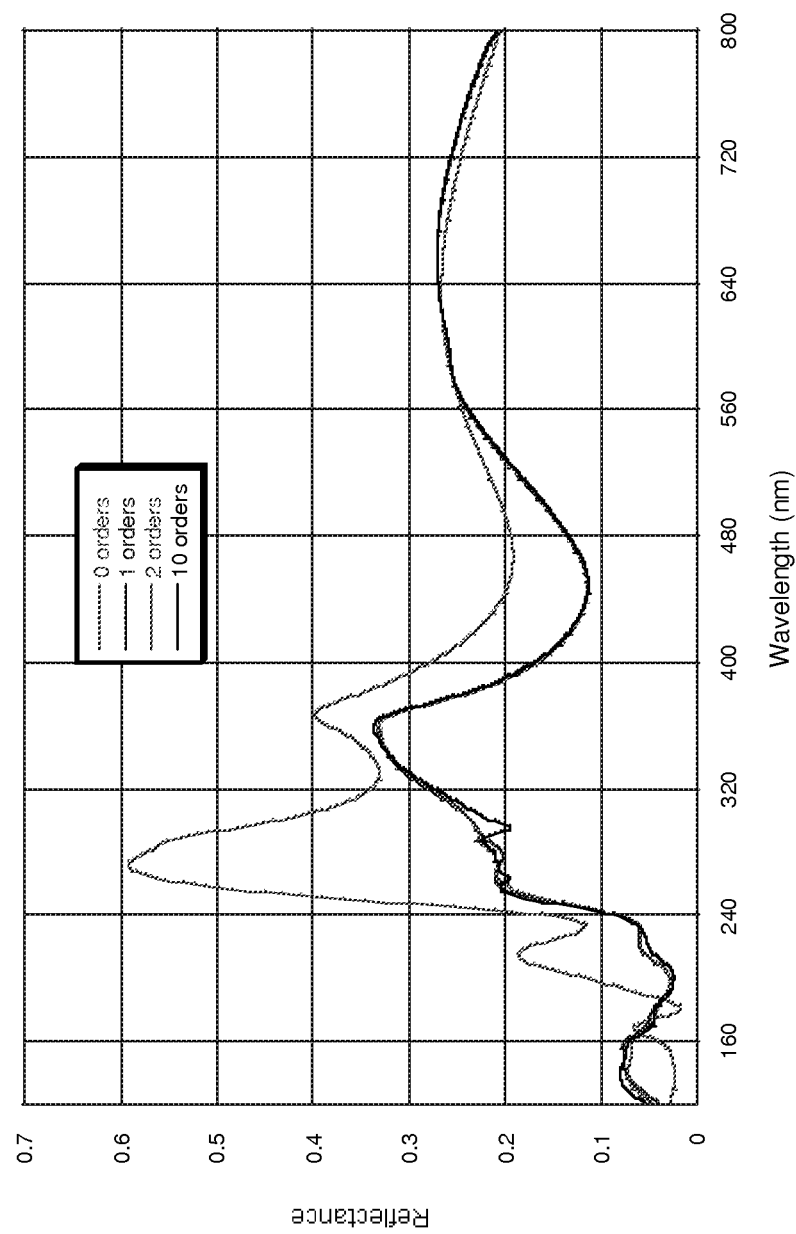
FIG. 6b shows a convergence simulation for a 640 nm pitch, 320 nm width, 77 nm height imprinted resist structure.
Figure 6C:
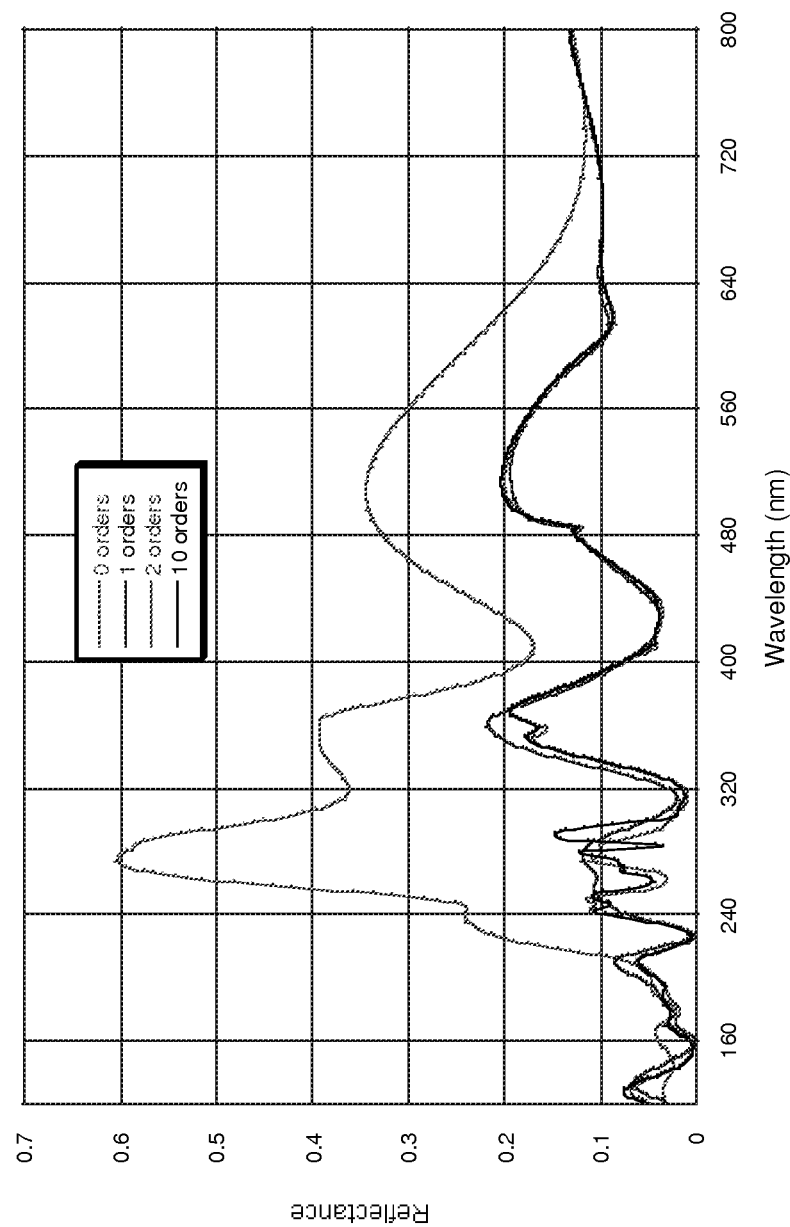
FIG. 6c shows a convergence simulation for a 640 nm pitch, 320 nm width, 200 nm height imprinted resist structure.

FIG. 6 illustrates convergence properties of calculated spectra for several imprinted resist structures. FIG. 6a compares 120-800 nm 0R reflectance spectra, calculated with 0, 1, 2, and 10 truncation orders, for a 64 nm pitch imprinted resist structure of 77 nm height, 32 nm width, 120 nm RLT, on a 60 nm adhesion under-layer on a silicon substrate. The figure shows that the spectra have fully converged with a truncation order of 1, and that a truncation order of 0 is nearly converged. There is very little difference between treating the structure as one having some lateral structure and one having no lateral structure at all. FIG. 6b shows a similar comparison, but for an imprinted resist structure scaled to 640 nm pitch, ten times as large. The width is scaled accordingly, but the height is kept the same at 77 nm. There is now a very large difference between the N=0 and N=1 calculations. FIG. 6c shows that as height of the large pitch structure is increased to 200 nm, the distinction between uniform and periodic structure becomes even greater, and more orders are required for full convergence of the spectra. FIG. 6 shows that the distinction between a film with no lateral structure and a layer having a grating structure with a lateral geometry depends on the grating dimensions compared to the incident wavelength, and that the distinction is much less for the smaller structures typical of the nanoimprint process.

Figure 7A:
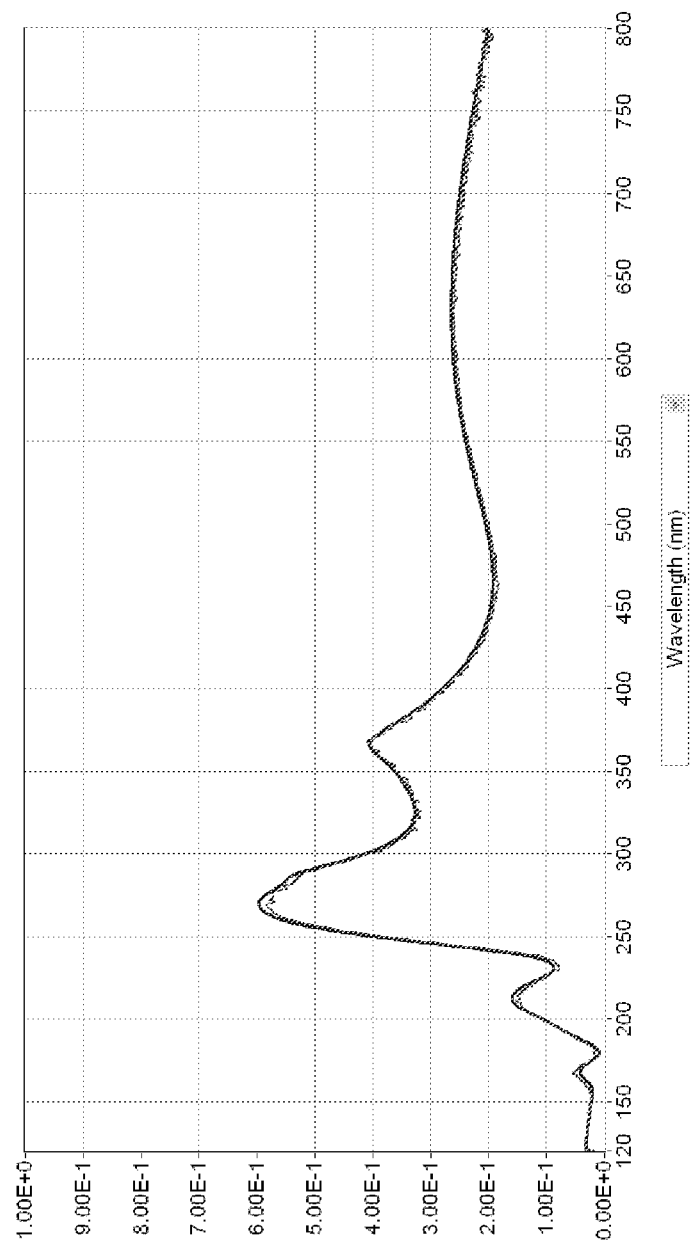
FIG. 7a shows a measured and RCW fit reflectance spectra for a nominally 64 nm pitch, 32 nm width, 77 nm height imprinted resist structure.
Figure 7B:
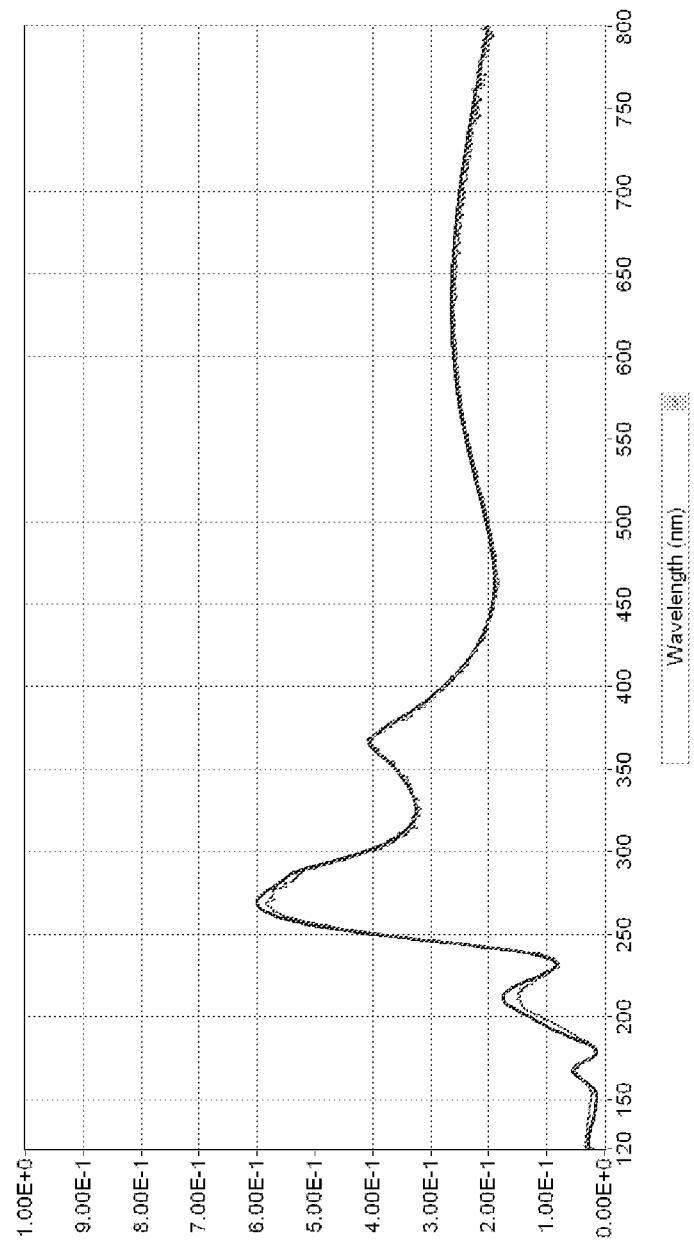
FIG. 7b shows a measured and EMA fit reflectance spectra for the nominally 64 nm pitch, 32 nm width, 77 nm height imprinted resist structure.

The result is that for the 64 nm pitch structure, the RCW method can be used efficiently with a very small number of orders. Alternately, since the structure is very similar to a laterally uniform film, an effective thin film thickness and refractive index measurement can be used. FIG. 7a shows an experimental reflectance and an optimal fit reflectance for an actual imprinted resist structure similar to the one simulated in FIG. 6. The model employed an RCW calculation with N=1, and a trapezoidal structure that varied height, top width, bottom width, and RLT. The regression result is 80.90 nm height, 28.91 nm top width, 36.99 nm bottom width, and 114.19 nm RLT. FIG. 7b shows the same experimental reflectance, but fit using a Bruggeman effective medium approximation that varied height, volume fraction, and RLT. The average width is computed by multiplying the pitch by the volume fraction. The result is 77.81 nm height, 31.06 nm average width, and 116.83 nm RLT.

Thus some embodiments of the present invention advantageously utilize the thin film analogy to simplify the analysis of the nanoimprint structures. Additionally, the thin film analogy can be exploited to simplify analysis of the interaction of the various optical components of the system with polarizing measurement samples. In many cases the interactions between polarizing samples and polarizing optical components can be neglected completely. In other cases, a simplified analysis of the interactions is sufficient.

Likewise, the interaction of a high numeric aperture focusing objective with a grating sample can be ignored or taken into account using simplified angle averaging. In one embodiment of the present invention, the final objective before the sample is a focusing objective designed to provide particular measurement spot characteristics at the sample surface. For example, the focusing objective could consist of an off-axis parabolic mirror with a suitable VUV-NIR reflective coating and with an off-axis angle of 90° as described in U.S. Pat. No. 7,126,131. The properties of the illumination spot on the sample are determined by the properties of the source and additional magnification optics, as well as the quality of the alignment of the system. However, for the purposes of embodiments of the present invention, our concern is with the range of angles incident on the sample, which is determined by the final objective.

In one embodiment, the final focusing objective can have a reflected effective focal length of approximately 6 inches and a clear aperture of approximately 1 inch, leading to a small range of angles incident on the sample about the sample normal. For all practical purposes the incident angle on the sample can be considered to be zero. In a second embodiment, the focusing optic has a reflected effective focal length of approximately 1 inch and a clear aperture of approximately 1 inch, leading to a larger range of angles incident on the sample, up to ~30 degrees. For the VUV reflectometer systems in U.S. Pat. Nos. 7,067,818 and 7,126,131 the incident light is approximately un-polarized and fills the entire objective surface. The resulting angles at sample surface are approximately distributed about a cone (azimuthal symmetry), and the polarization effects of the objective are small and otherwise mostly average out.

Figure 8A:
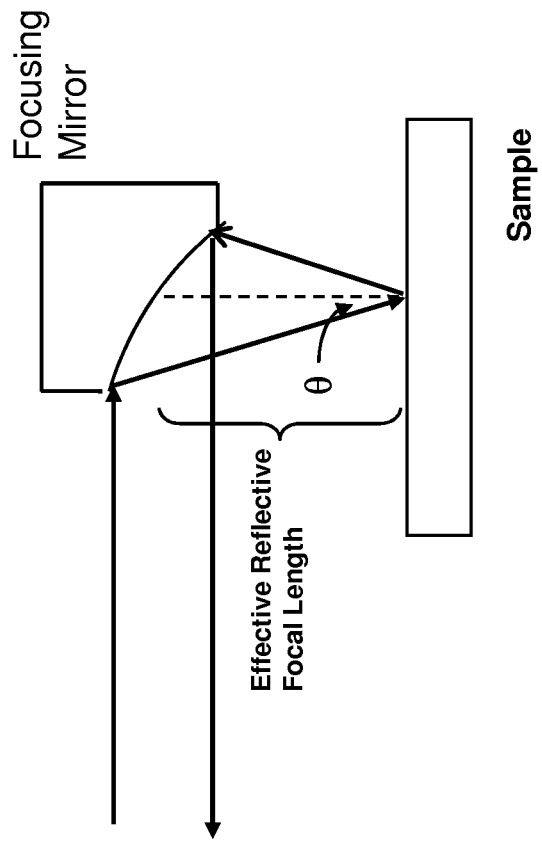
FIG. 8a shows a schematic of a focusing objective used in one embodiment of the present invention.
Figure 8B:
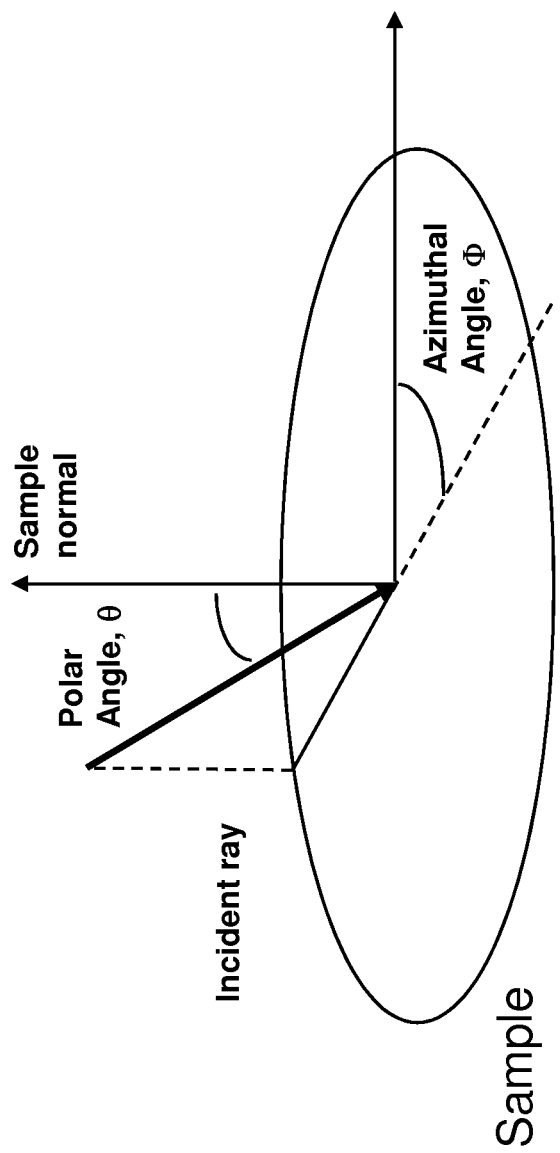
FIG. 8b shows a schematic defining angles of incidence with respect to a measured sample.

FIG. 8a shows a schematic of a large NA objective relative to a sample. The angle of incidence on the sample, as defined in FIG. 8b, is determined by the position of the sample relative to the mirror, and the location on the mirror surface from which the incident ray originates. FIG. 8a shows a single incident ray for clarity, but in the embodiments described above, collimated light fills, or nearly fills the entire objective plane. Therefore, there is a distribution of incident angles on the sample. For a given mirror, this distribution can be determined from the parabolic geometry and the mirror's focal length, and consists of pairs of polar (theta) and azimuthal (phi) values, along with a relative weighting for each theta/phi pair. The actual measured reflectance is the normalized weighted average of the angle of incidence distribution.

Figure 8C:
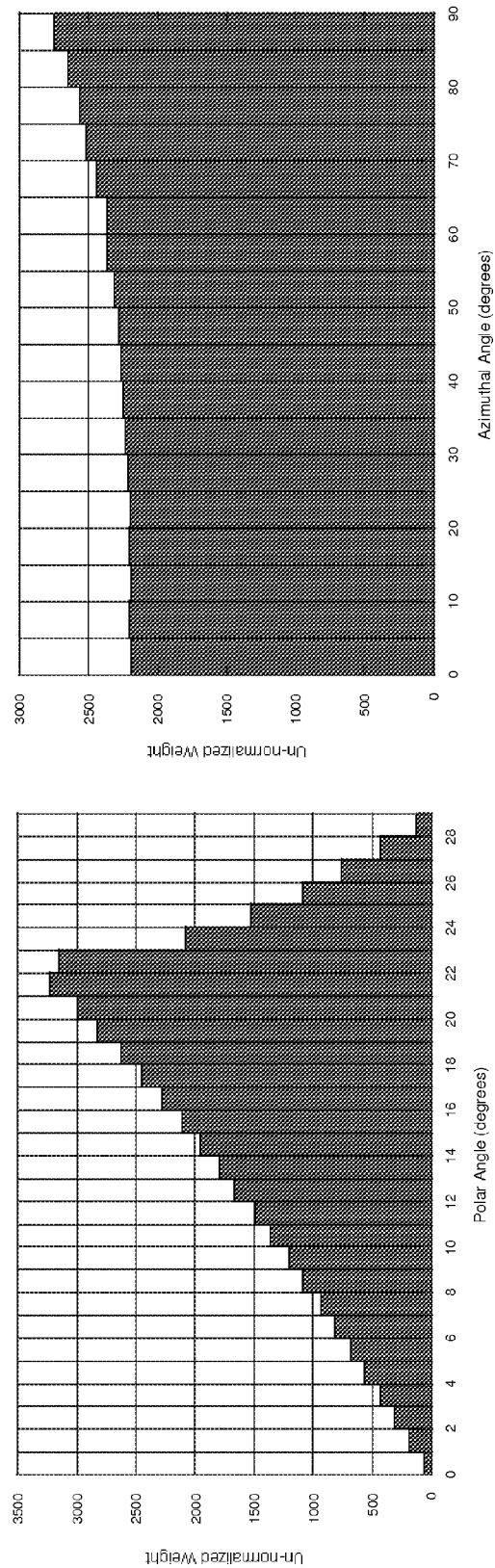

FIG. 8c shows polar and azimuthal projections of the angle of incidence distribution for a 1-inch reflected effective focal length (parent focal length ½ inch). From FIG. 8c, it is clear that the polar distribution (angle from normal) is sharply peaked at 21-22°, with weighted average of ~17°, while the azimuthal distribution is nearly uniform. For samples whose reflectances are not strongly dependent on the angle of incidence, it may suffice to assume a single, effective angle of incidence. For line/space structured samples (gratings) there may be an azimuthal dependence, in which case a single effective polar angle may be averaged over multiple azimuthal angles.

Figure 9:
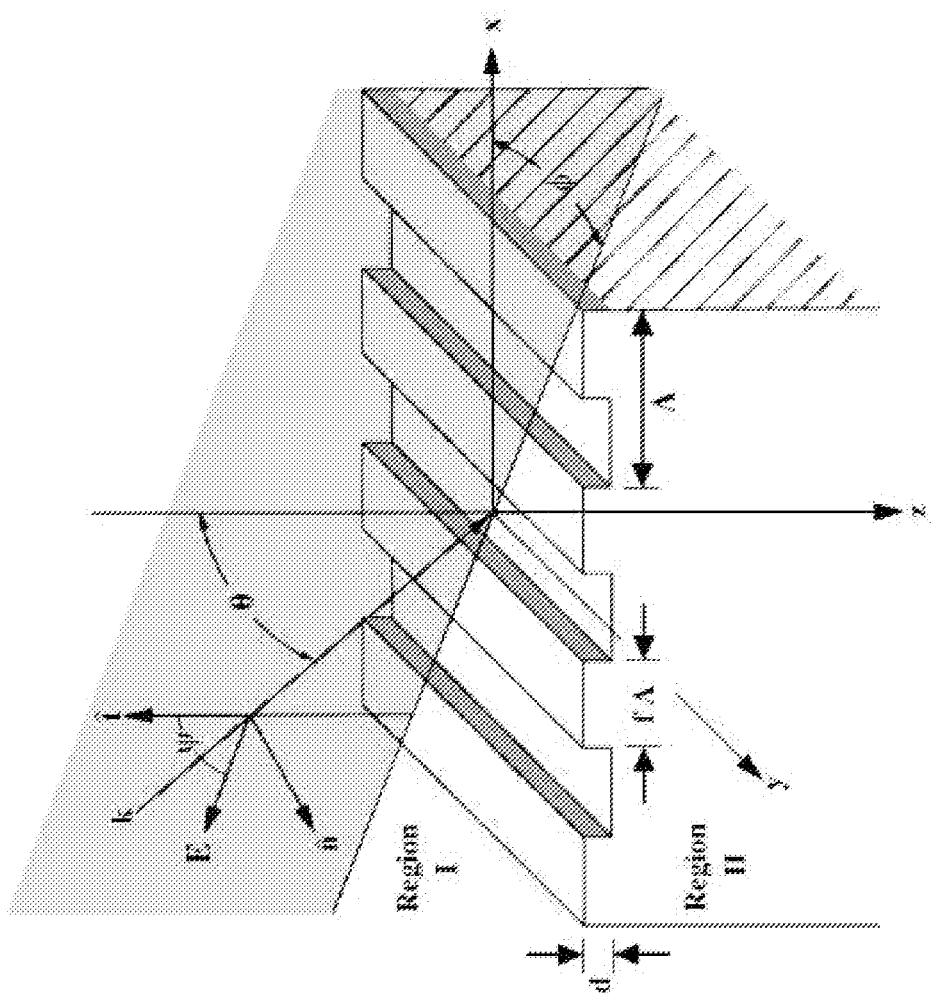
FIG. 9 is schematic illustrating polar (theta) and azimuthal (phi) incident angles with respect to a grating sample structure.

In order to extract structural information from the sample, an accurate model reflectance should be calculated. FIG. 9 shows a schematic of the angle of incidence and polarization definitions typically used for grating calculations. It is evident that if the grating sample is oriented so that the lines/spaces are perpendicular to the plane shown in FIG. 8a, the polar angle, theta, and azimuthal angle, phi can be mapped from the angle of incidence distribution due to the focusing objective directly onto the angle of incidence used for the grating calculation.

While the azimuthal angle ranges from 0 to 360 degrees, in FIG. 8c the azimuthal weightings have all been mapped onto the 0-90 degree range. This is appropriate for a line/space grating structure, since it has mirror symmetry about both parallel and perpendicular axes. For example, when the grating is oriented so that an azimuthal angle of 0 corresponds to a plane of incidence perpendicular to the grating lines, azimuthal incidence angles of 85, 95, 265, and 275 degrees all result in the same reflectance, and similarly for azimuthal angles of 5, 355, 175, and 185 degrees. Therefore FIG. 8c gives the total weights of azimuthal angles that lead to unique reflectances for a line/space grating structure.

In theory, the calculated reflectance would have to take into account all of the possible angle of incidence conditions. However, for nanoimprint structures this time-consuming step normally does not have to be fully implemented. Reflectance spectra for typical nanoimprint structures can be simulated using the full angle of incidence distributions, and the simulated spectra used to test various approximate angle averaging schemes.

FIG. 10 shows simulations of a quartz template reflectance using the full predicted angle of incidence distribution and various approximate angle of incidence distributions. The template parameters are 120 nm pitch, 65 nm depth, 45 nm top width, and 70 nm bottom width. The un-polarized reflectances in FIG. 10 are calculated from the average reflectance of light incident at two orthogonal polarizations according to $$R = \tfrac{1}{2}(R_S + R_P)$$ Eq. 9 for each incident theta and phi pair, where the subscript s corresponds to light polarized perpendicular to the incident plane ($\Psi = 90°$ in FIG. 9), and p to light polarized parallel to the incident plane ($\Psi = 0°$ in FIG. 9). The un-polarized reflectances are then averaged according to the weighted distribution shown in FIG. 8c, or by using a simpler distribution as described below.

Figure 10A:
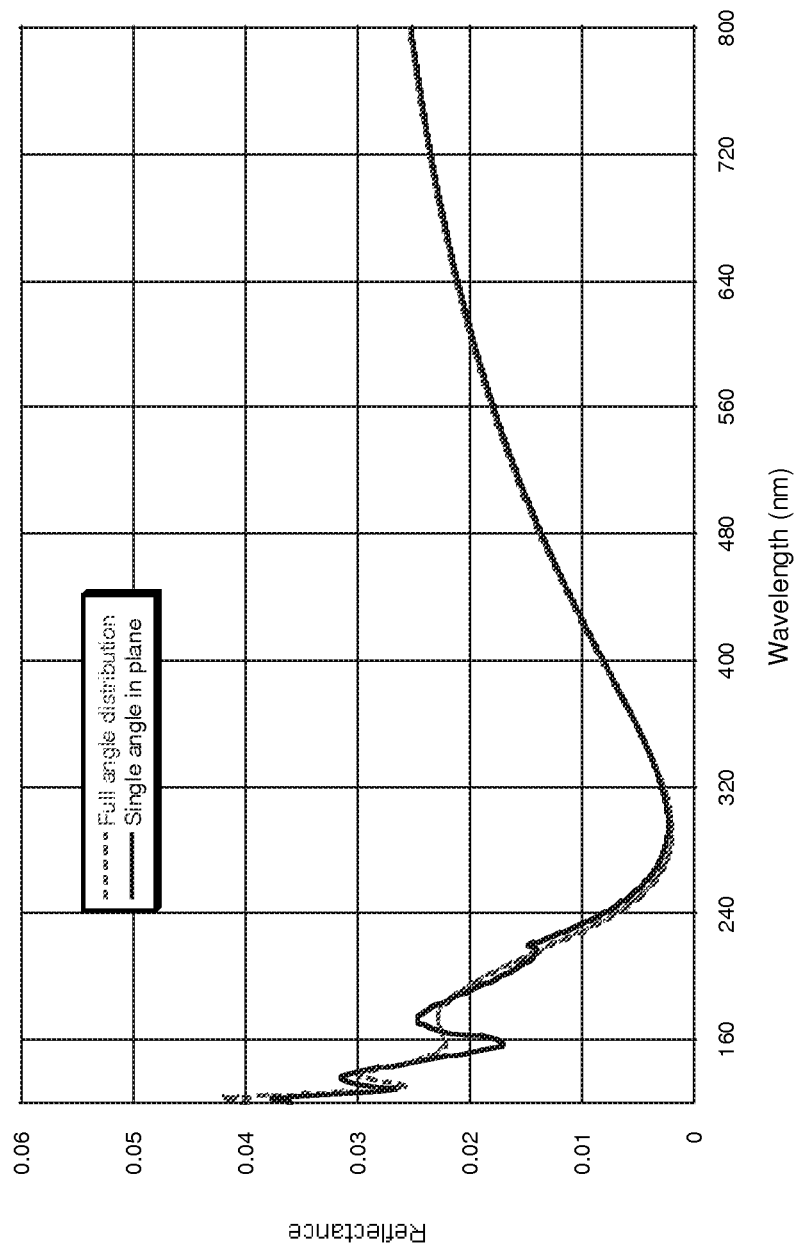
FIG. 10a shows simulations of a quartz template reflectance performed using the full theoretical angle of incidence distribution of one embodiment of the focusing objective of FIG. 8 (dashed line) with a simulation of the same grating assuming a single angle of incidence.
Figure 10B:
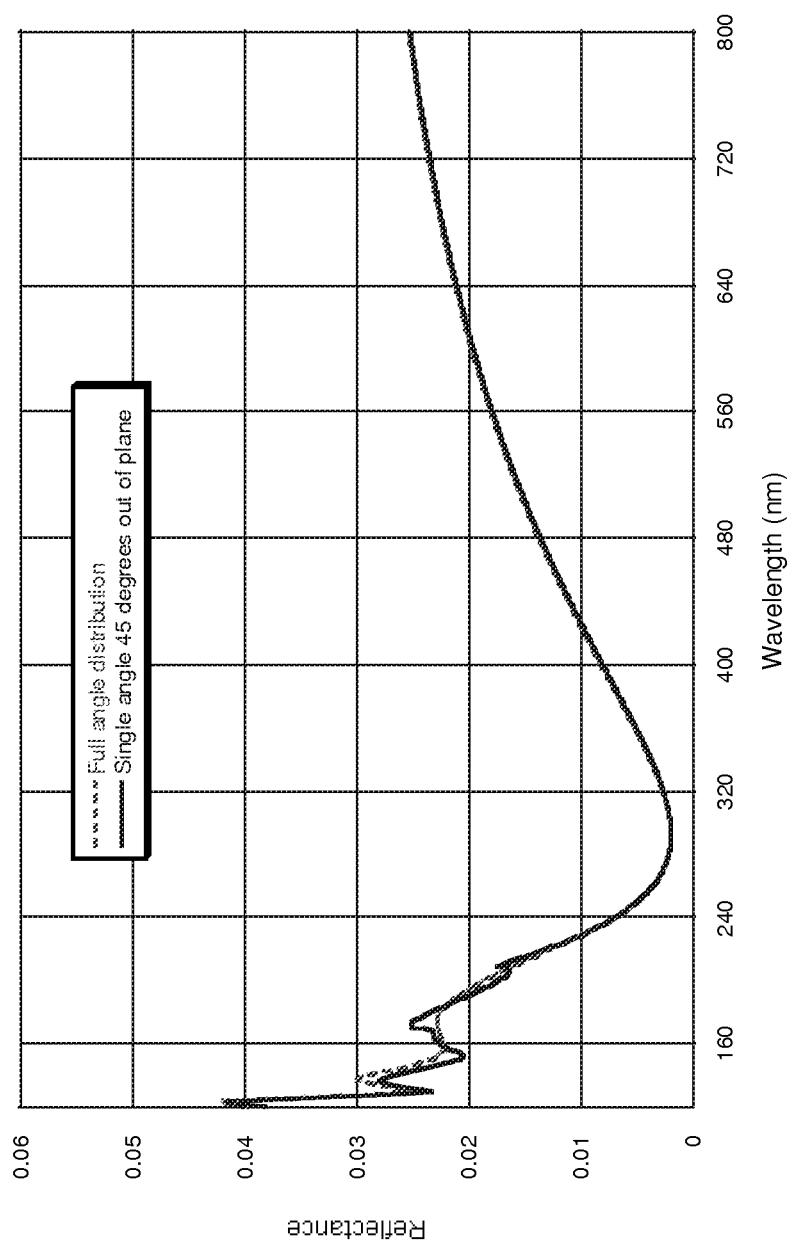
FIG. 10b shows simulations of a quartz template reflectance performed using the full theoretical angle of incidence distribution (dashed line) with a simulation of the same grating assuming a single angle of incidence, but with an azimuthal angle of 45 degrees.
Figure 10C:
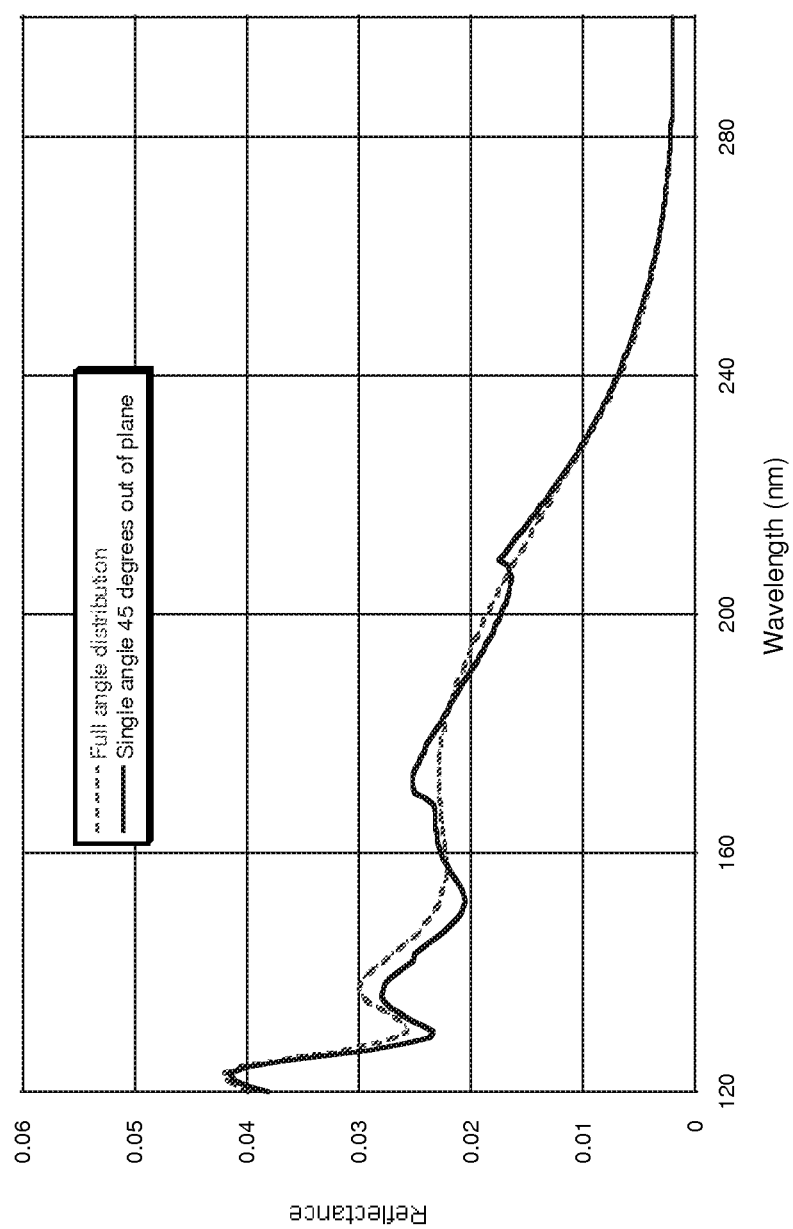
FIG. 10c shows a view of FIG. 10b, expanded to emphasize the 120-300 nm wavelength region.
Figure 10D:
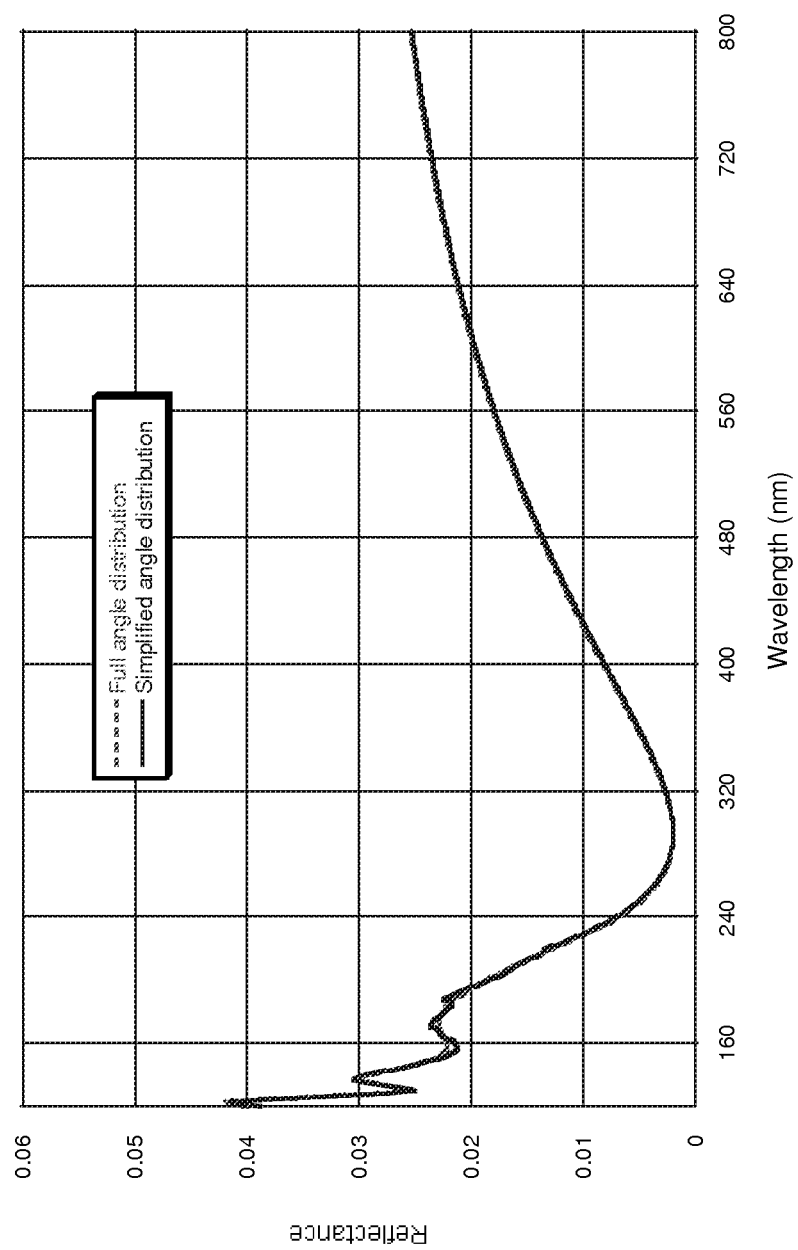
FIG. 10d shows simulations of a quartz template reflectance performed using the full theoretical angle of incidence distribution (dashed line) with a simulation of the same grating assuming a simplified angle of incidence distribution.

FIG. 10a compares the full angle distribution with a single, in-plane (azimuthal angle zero) angle of incidence of 17°. Note that reflectance is plotted on a normalized scale, and can range from 0 to 1. From the figure, the overall shape of the spectrum is reproduced by the single-angle simulation, but much of the fine detail is not. FIG. 10b compares the full distribution with a single angle at 17° polar, and 45° azimuthal angle. The agreement is closer than in FIG. 10a. FIG. 10c shows a view zoomed in to the 120-300 nm wavelength range, where some fine detail is still significantly different. FIG. 10d shows a comparison between the full distribution and a simplified out-of-plane averaging of equal parts 0, 45, and 90 degree azimuthal angles, all at 17° polar angle. The expanded view in FIG. 10e shows that this simplified distribution recovers nearly the entire full-distribution spectrum, including the significant fine detail.

Figure 10E:
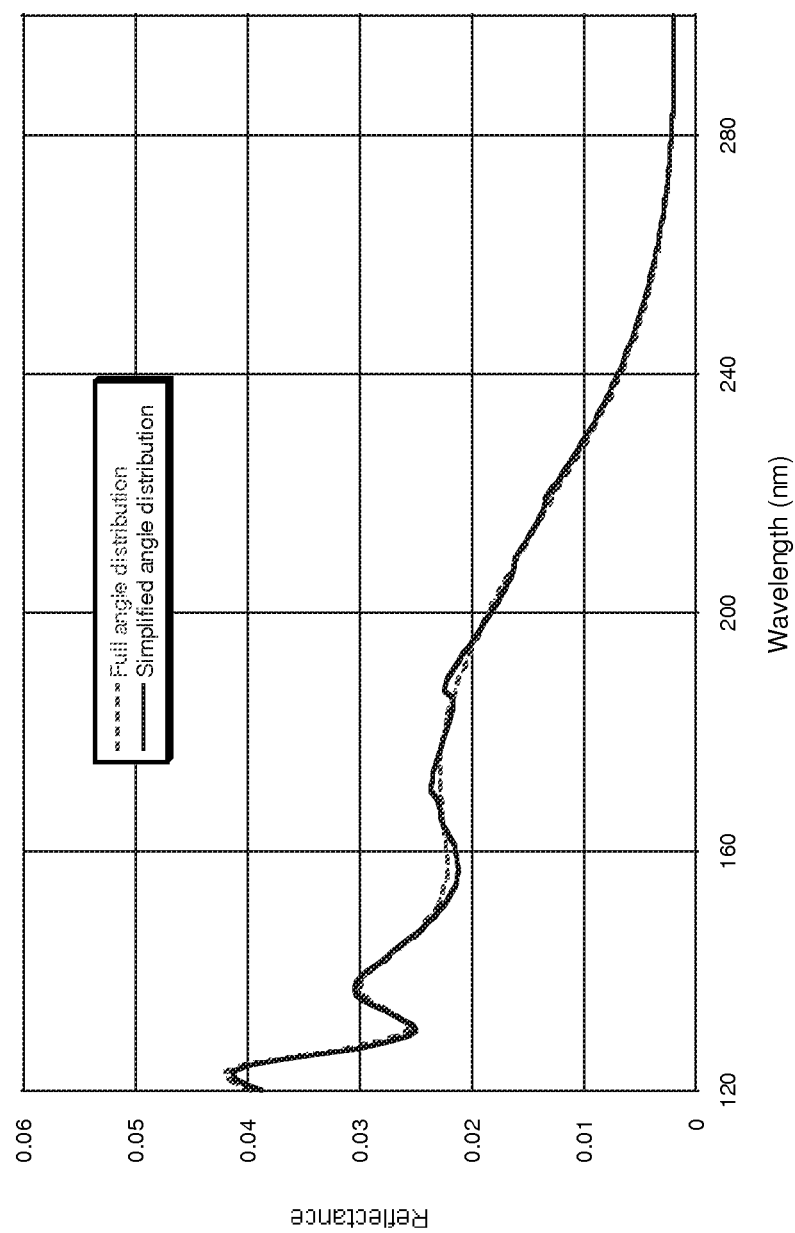
FIG. 10e shows an expanded view of FIG. 10d, emphasizing the 120-300 nm wavelength region.

The simplified angle distribution shown in FIGS. 10d and 10e can be used to significantly speed up the analysis step of the metrology measurement when using the focusing objective of FIG. 8, since only three angle of incidence conditions need to be calculated in order to generate an accurate reflectance spectrum. Further speed-up can be achieved by making use of the symmetry of the 0 and 90 degree azimuthal incident calculations. The algorithms given in Moharam (1995) already take the symmetry into account for the planar (phi=0) diffraction case. For the 90 degree azimuth case (phi=90), the methods provided in U.S. patent application Ser. No. 12/592,773, incorporated herein by reference, can be employed, reducing the calculation for that case to a speed comparable to the phi=0 case. This leaves one full conical calculation at 45 degree azimuth, and two reduced calculations, at 0 and 90 degree azimuths, per spectrum calculation.

Figure 11A:
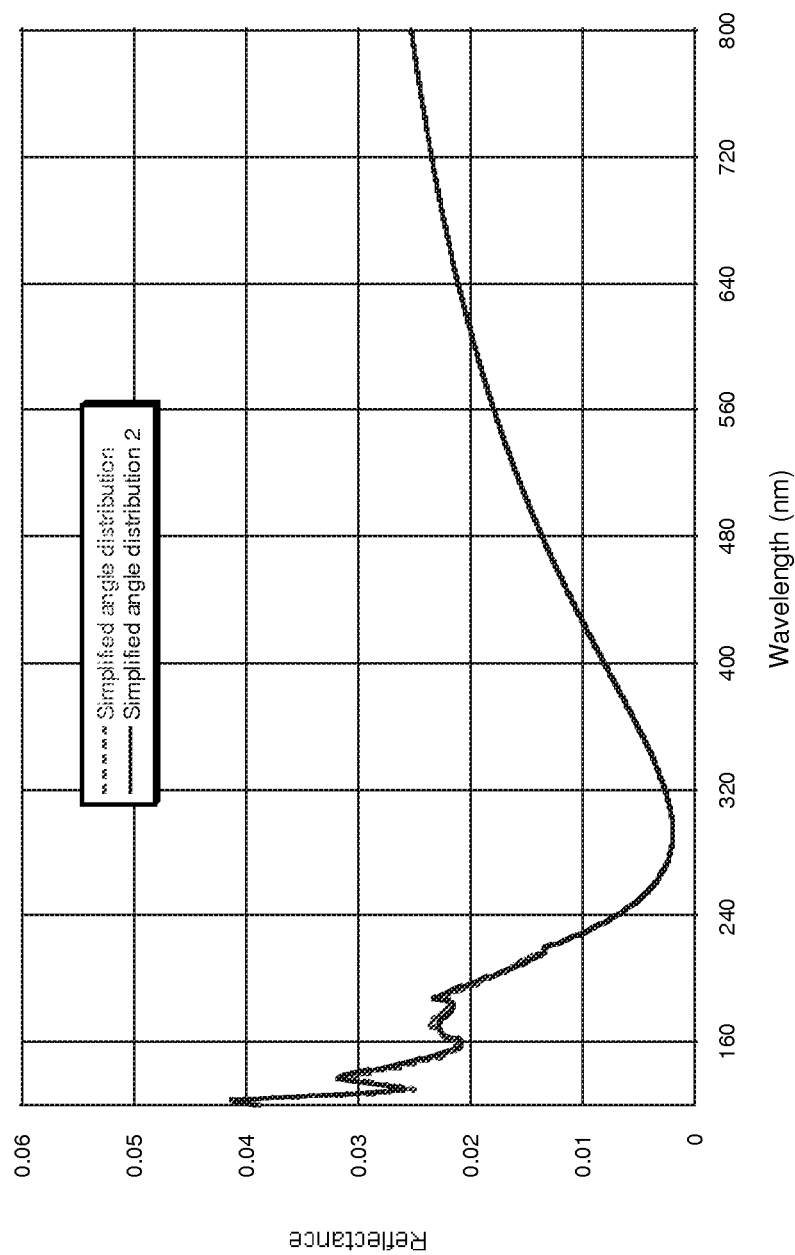
FIG. 11a shows a comparison of two simplified angle of incidence distributions for the template of FIG. 10 and one embodiment of the focusing objective of FIG. 8.
Figure 11B:
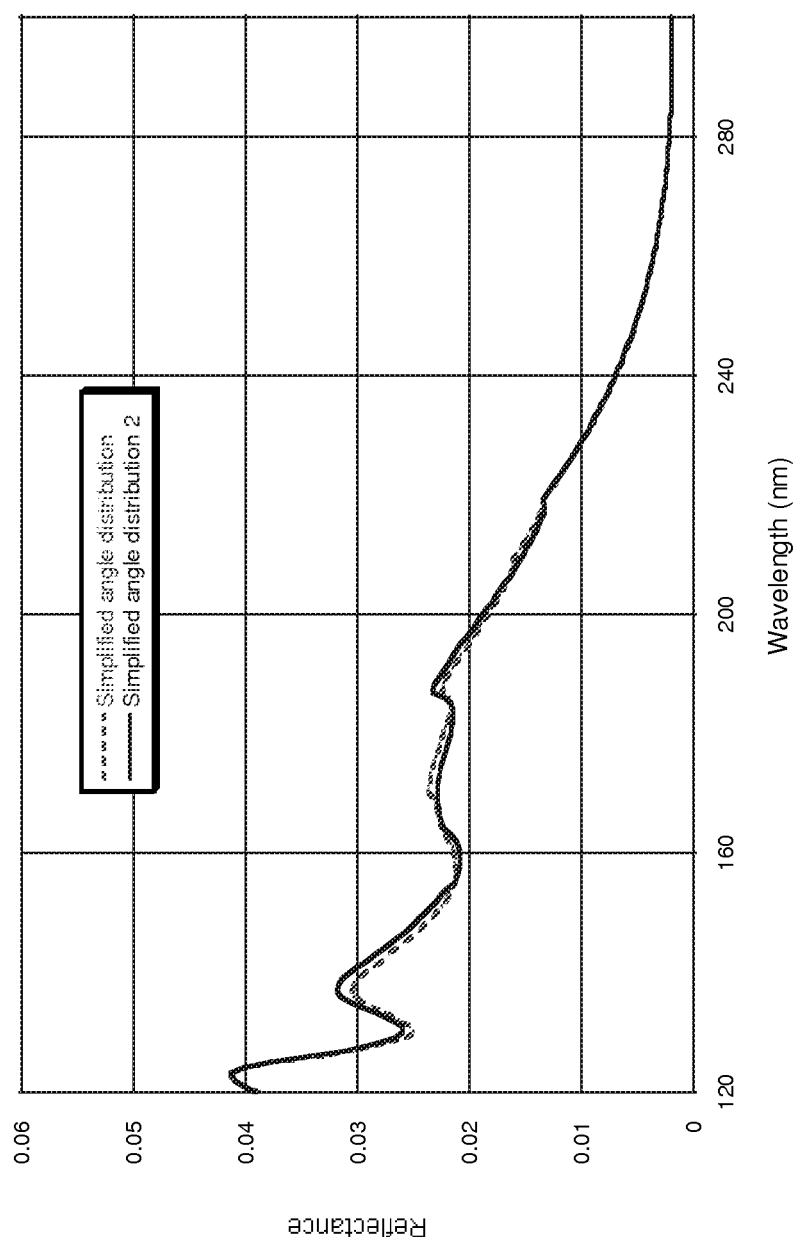
FIG. 11b shows an expanded view of FIG. 11a emphasizing the 120-300 nm wavelength region.

Still further speed enhancements can be realized by making use of the wavelength-dependence of the angle of incidence sensitivity for a given structure. For example, FIGS. 10b and 10c show that a single angle of incidence calculation is sufficient at wavelengths above ~250 nm. For the case shown in FIG. 10, a calculated reflectance spectrum can consist of an averaged calculation of three angles in the region 120-250 nm, along with a single angle calculation for the 250-800 nm region. The metrology tool analysis software can automatically keep track of which wavelengths are calculated using a given angle of incidence distribution. FIG. 11 shows a comparison between the three-angle spectrum from FIG. 10d and FIG. 10e and an even simpler distribution consisting of just the average of the phi=0 and phi=90 azimuth calculations (Simplified angle distribution 2). This provides a further speed enhancement to the above as the phi=45 degree calculation is roughly a factor of 8 slower than the phi=0 and phi=90 calculations. For the case in FIGS. 10 and 111, the calculation may average three angles from ~120-220 nm, and the two orthogonal 0 and 90 degree azimuthal angles from 220-800 nm.

The angle of incidence distribution used for reflectance calculations can be configured to be recipe-dependent. For example, the template case shown in FIG. 10 is actually one of the more extreme cases of those typically encountered. Structures having smaller pitch and especially imprinted resist structures are much less sensitive to different angle of incidence conditions. In most cases, there is very little difference in the analyzed results when using a single, effective angle of incidence versus the full theoretical distribution. Therefore, along with nominal film/structural information about a particular nanoimprint structure, an analysis recipe will also contain information about how to do the angle averaging for that particular structure. The result is that the angle of incidence distribution is taken into account only to the extent necessary for a given structure and incident wavelength condition. For structures and incident conditions that are not very sensitive to incident angle, a single effective angle of incidence is used.

When measuring polarizing samples with a reflectometer, it is often desirable that the incident light be un-polarized, and that the optical path itself not impart an additional polarization dependence on either the incident or reflected light, at least to the extent that is practical. Optical components, such as beam splitters, windows, and mirrors can be chosen such that latent polarization of the optical system is minimized. Depolarizers can be used to counter the effects of polarizing optics or detection systems. Additionally, there are methods for constructing optical systems, such as placing successive mirrors in orthogonal optical planes, such that the effective polarization on the light is negligible, even when the individual optical components impart some polarization dependence.

Detectors and spectrophotometers can also be chosen so that polarization effects are minimized. Spectroscopic instruments often utilize gratings in order to separate measured light into its constituent wavelengths. Depending on its structure and material composition, the efficiency of a grating can be strongly polarization dependent. In the extreme case that the sample and grating spectrometer are both strongly polarizing, the measured response is expected to be strongly dependent on the sample orientation. One embodiment of the present invention incorporates an approximately non-polarizing LiF prism spectrometer, such as that taught in U.S. Pat. No. 7,485,869 incorporated in its entirety by reference, in place of the grating spectrometer, in order to minimize the polarization effects of the detection system. The prism spectrometer of U.S. Pat. No. 7,485,869 has the additional advantage of enhanced detection efficiency compared to a traditional grating spectrometer.

Optical coatings of mirrors and beam splitters can be chosen so as to impart negligible polarization on reflected and transmitted light beams. Additionally, materials for beam splitters and windows can be chosen such that polarization due to birefringence is minimized. Accordingly, one embodiment of the present invention replaces magnesium fluoride beam splitters and windows with lithium fluoride beam splitters and windows. Aside from polarization effects, this substitution has the added benefit that the minimum transmission wavelength is further reduced—to ~105 nm for LiF, compared to ~114 nm for $MgF_2$.

For polarizing line/space samples, the effect of latent polarization of the optical system is to define a reference frame for the sample polarization. This results in a sample orientation dependence of the detected light, since the sample orientation modifies the polarization state of the light with respect to the optics plane. In the idealized case that polarization effects of the optical system are completely eliminated, there is no orientation dependence due to sample polarization, even for a strongly polarizing sample. Likewise, if the optical system polarizes, but the sample does not, sample orientation dependence is eliminated. In either case, when un-polarized input light is used, and the sample reflected intensity is normalized using a non-polarizing calibration sample of known reflectance, the result is $$R = \tfrac{1}{2}(R_{TE} + R_{TM}), \qquad \text{Eq. 10}$$

where $R_{TE}$ and $R_{TM}$ are defined with respect to the phi=0 sample incidence configuration, regardless of sample orientation.

As previously mentioned, nanoimprint structures are not as strongly polarizing at typical measurement wavelengths as would be similar, but larger structures. This reduces the constraint on the latent polarization of the optical system—i.e., more latent polarization can be tolerated, and Eq. 10 practically applies. As in the case of angle of incidence considerations, for many nanoimprint structures polarization effects can be ignored completely. The validity of this approximation for a given structure can be tested by recording the reflected intensity from the structure for several different sample orientations, preferably including 0 and 90 degree orientations, with respect to the optics plane. If the spectra are similar, then the polarization effects can be ignored.

In some cases, the sample and optics may polarize at some wavelengths such that a small effect is observed at those wavelengths. Often, the polarization is weak enough that interaction between sample and optics is dominated by a single optical component, either in the source side or detection side. Practical examples could include the grating spectrometer, or transmission through a beam splitter or window. For a single polarizing optical component on the detection side, the detected intensity is proportional to $$I \propto \tfrac{1}{4}(T_S + T_P)(R_{TE} + R_{TM})\{1 + \cos 2\phi \cos 2\Psi_S \cos 2\Psi_D\}, \qquad \text{Eq. 11}$$

where $\tfrac{1}{2}(T_S + T_P)$ is the reflectance/transmittance magnitude of detection side optics, $\tfrac{1}{2}(R_{TE} + R_{TM})$ is the un-polarized reflectance of the sample, and $\phi$ is the azimuthal orientation angle of the sample with respect to the optics plane. As an example, if the sample structure consists of a 1-D line/space grating structure, $\phi$ is the angle between the plane perpendicular to the line/space grooves and the plane defined by the optics. In one embodiment, the optics plane is defined by the plane of reflection/transmission of the beam splitter and mirror M-2 of FIG. 5. $\Psi_S$ and $\Psi_D$ are the ellipsometric parameters of the sample and polarizing optic, defined by $$\tan\Psi_S = \sqrt{\frac{R_{TM}}{R_{TE}}} \qquad \text{Eq. 12}$$

and $$\tan\Psi_D = \sqrt{\frac{T_P}{T_S}}, \qquad \text{Eq. 13}$$

respectively. Equations 10-13 are used without loss of generality in the sense that the single optic could be replaced by multiple successive optics sharing the same optics plane, or the polarizing optic could also occur on the source side instead of the detection side. The intensity for a non-polarizing reference sample is proportional to $$I_{Cal} \propto \tfrac{1}{2}(T_S + T_P)(R_{Cal}),$$

so that the calibrated reflectance is $$R' = \left(\frac{I}{I_{Cal}}\right)R_{Cal} =$$
$$\frac{1}{2}(R_{TE}+R_{TM})\{1+\cos 2\phi \cos 2\psi_S \cos 2\psi_D\} = A_0 + A_1 \cos 2\phi, \quad \text{Eq. 14}$$

where $$A_0 = \tfrac{1}{2}(R_{TE}+R_{TM}) \quad \text{Eq. 15}$$

and $$A_1 = \tfrac{1}{2}(R_{TE}+R_{TM})\cos 2\psi_S \cos 2\psi_D \quad \text{Eq. 16}$$

assuming the reflectance of the reference sample, $R_{Cal}$, is known (i.e., one measures I and $I_{Cal}$, and multiplies the ratio $I/I_{Cal}$ by the known reflectance $R_{Cal}$).

Equations 11-16 are strictly valid for a normal incidence configuration. However, if the primary cause of sample polarization is due to the line/space structure, then a focusing objective like the one shown in FIG. 8 can be treated similarly. This is equivalent to saying that the polarization due to the top-down sample structure is more significant than polarization due to a finite sample angle of incidence distribution like the one shown in FIG. 8, which is true of nanoimprint structures. Therefore, when considering polarization effects, the finite spread of angles about the sample normal caused by using a focusing objective is ignored and polarization effects are considered to be decoupled from angle of incidence effects. When analyzing reflectance from the sample, the effective angle of incidence or simplified angle of incidence distribution are used whenever the quantity $\tfrac{1}{2}(R_{TE}+R_{TM})$ is calculated.

For small sample and/or optic component polarization effects, the product $\cos 2\Psi_S \cos 2\Psi_D$ is very small, so that $$R' = \tfrac{1}{2}(R_{TE}+R_{TM})\{1+\cos 2\phi \cos 2\psi_S \cos 2\psi_D\} \approx \tfrac{1}{2}(R_{TE}+R_{TM})=R. \quad \text{Eq. 17}$$

In other words, polarization effects are negligible, and the measured reflectance is $\tfrac{1}{2}(R_{TE}+R_{TM})$, regardless of sample orientation. For many nanoimprint samples, polarization effects are small enough so that Eq. 17 can be used. Sample polarization effects are smaller for smaller pitch structures, and for a given pitch tend to be smaller for nanoimprint structures than for the corresponding template structures.

Figure 12:
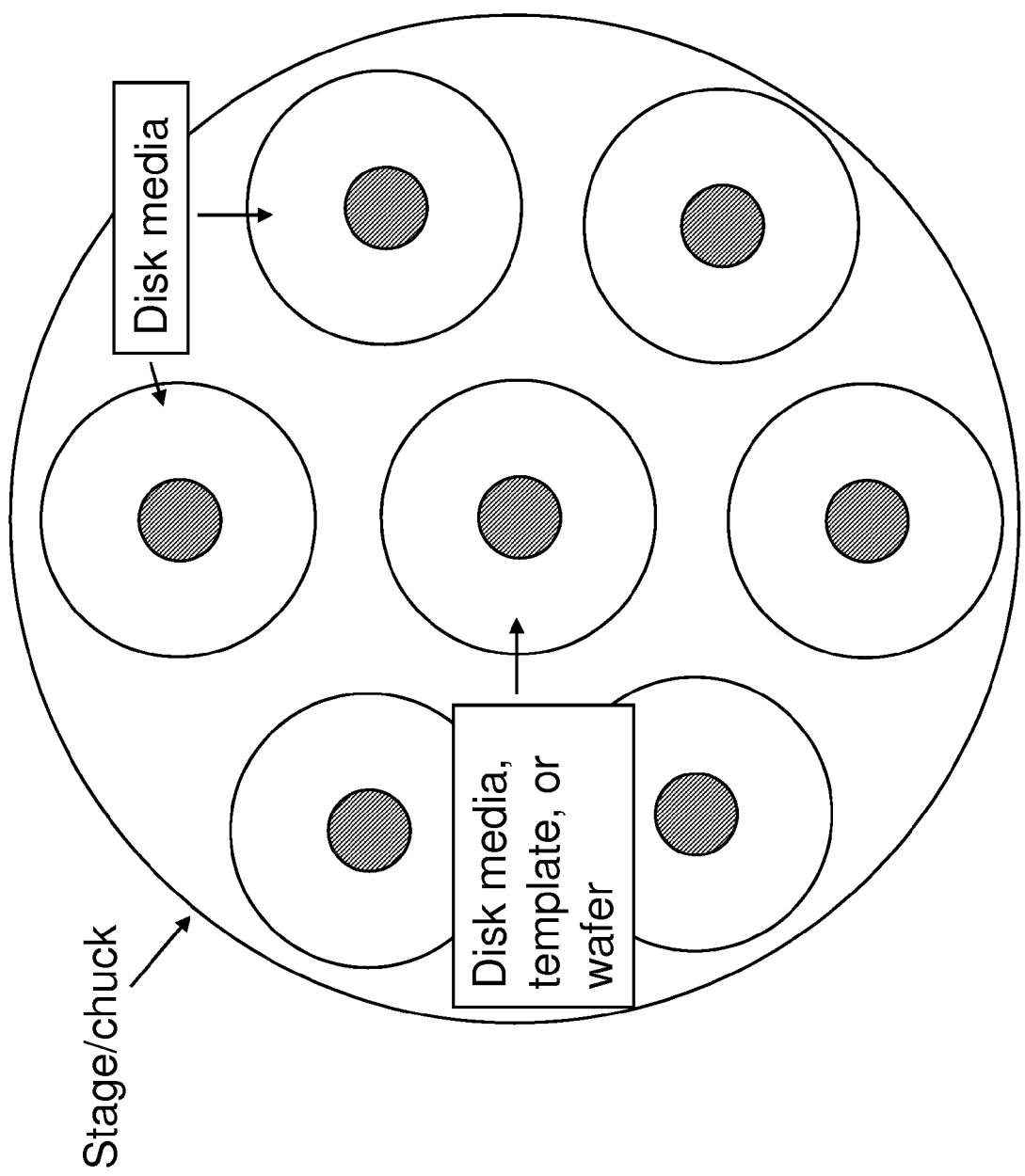
FIG. 12 illustrates a sample holder for use with one embodiment of the present invention.

When the factor $\cos 2\Psi_S \cos 2\Psi_D$ is significant, the orientation dependence can be removed by simply aligning the sample at the same orientation with respect to the optical plane for every measurement. This has the effect of maintaining a constant value for $\phi$ in Eq. 11 or Eq. 14. In the case of DTR media, the tracks are normally concentric around the substrate disk. If the sample is mounted on an r-θ stage such that its center is aligned with the center of rotation of the stage, the lines/spaces will always be aligned in the same direction, regardless of where the sample is measured. A chuck design is illustrated in FIG. 12 that incorporates a sample holder that can mount 6 orientation-independent samples around the circumference of the chuck, and a seventh sample can be positioned so that its center is aligned with the center of rotation of the r-θ stage. Different samples can be mounted according to whether or not they are expected to exhibit orientation-dependence. An x-y stage having an additional rotational degree of freedom, commonly referred to as an x-y-θ stage, could also be used. A measurement recipe would then include x and y location coordinate, as well as an orientation, for every measurement point.

The orientation dependence can be experimentally probed by collecting a series of reflected intensity scans at one location of a sample, but for several different orientations. Generally, if a sample of a particular type does not exhibit orientation dependence, then it is safe to assume that all samples of that type that differ by normal process variation are "safe" to mount in the orientation-independent locations. This means that an orientation test need only be done once on a small set of samples for a given nominal structure, and that subsequent samples having the same nominal structures can be placed as appropriate according to the results of the orientation experiment. For example, a nanoimprint sample of a given pitch may not exhibit orientation dependence, while the corresponding quartz template does. For process control using an embodiment of the present invention, the tool operator might then mount all nanoimprint samples of that pitch at the orientation-independent locations, but always mount the template sample at the center, constant orientation position.

Referring again to Eq. 14, there are special orientations that lead to polarization-independent results, regardless of the magnitude of $\cos 2\Psi_S \cos 2\Psi_D$. When $\phi=45°$, so that $\cos 2\phi=0$, Eq. 14 becomes $$R' = \tfrac{1}{2}(R_{TE}+R_{TM})=R. \quad \text{Eq. 18}$$

Also, $\cos[2(\phi+90)]=-\cos(2\phi)$, so that $$\tfrac{1}{2}(R(\phi)+R(\phi+90)) = \tfrac{1}{2}[\tfrac{1}{2}(R_{TE}+R_{TM})\{1+\cos 2\phi \cos 2\psi_S \cos 2\psi_S\}+\tfrac{1}{2}(R_{TE}+R_{TM})\{1-\cos 2\phi \cos 2\psi_S \cos 2\psi_D\}] = \tfrac{1}{2}(R_{TE}+R_{TM})=R \quad \text{Eq. 19}$$

Equation 18 says that polarization effects can be completely removed from the measurement by aligning the sample so that the lines/spaces lie at a 45° orientation angle with respect to the plane of the optics. Equation 19 gives a method for removing polarization effects without the need to align the sample with respect to the optics plane, as long as two orthogonal measurements are averaged. One embodiment of the present invention achieves this using an x-y-θ stage. The sample can be mounted anywhere and the sample grating lines can run in any direction. For each measurement, the stage travels to a given x-y coordinate and collects a first reflectance spectrum. Then the sample is rotated so that the sample grating lines and spaces are oriented in an orthogonal direction compared to the first scan, and a second spectrum is collected. The sample-dependent reflectance is then the average of the two measured spectra.

In another embodiment, a known polarizing sample can be used to estimate the value of $\cos 2\Psi V_D$. One method for doing this is to measure the sample at a 45 degree orientation, analyzing $\tfrac{1}{2}(R_{TE}+R_{TM})$ to find the sample properties, and then collecting data at a different orientation, say 0 degrees, and solving for $\cos 2\Psi_D$ from Eq. 14, since $\cos 2\Psi_S$ can be calculated from the sample properties. For subsequent measurements of unknown samples, a standard reflectance measurement is performed, which is actually a measurement of R'. However, since the sample orientation, $\phi$, is known from the sample nominal structure and the stage position, and $\cos 2\Psi_D$ is known from the calibration procedure, the regression procedure can be done on the quantity R' instead of R, where now at each regression step $R_{TE}$, $R_{TM}$, and $\cos 2\Psi_S$ are calculated assuming the line/space parameters at that step. This is in contrast to a standard reflectance analysis using $R_{TE}$ and $R_{TM}$.

The sample used for the calibration should have a structure that is easy to analyze and is well-characterized by a small number of parameters—e.g. height, average width, and sidewall angle. A quartz template or $SiO_2$ lines on silicon are good choices. It is also beneficial to have a significantly polarizing calibration sample, to best probe the properties of cos $2\Psi_D$. Therefore, a good choice for a calibration sample may consist of gratings of larger pitch than typical nanoimprint samples.

On the other hand, Eq. 14 is strictly valid when only source or detection side optics, but not both, are polarizing. If both source and detection optics polarize, but one has a stronger effect than the other, Eq. 14 may be approximately true when measuring weakly polarizing samples, but less accurate when measuring strongly polarizing samples. Therefore, experimentation may be necessary in order to determine the best calibration sample, i.e., one that exhibits only a cos $2\phi$ dependence on orientation, with no higher frequency ($3\phi$, $4\phi$, etc.) dependence on $\phi$.

Since cos $2\Psi_D$ must be determined for each wavelength, an alternate embodiment collects multiple data points from the calibration sample by rotating its orientation from 0 to 360 degrees. The resulting R' exhibits a cos $2\phi$ dependence, with the average being $\frac{1}{2}(R_{TE}+R_{TM})$, and the amplitude equal to $\frac{1}{2}(R_{TE}+R_{TM})\cos 2\Psi_S \cos 2\Psi_D$. Again, $\frac{1}{2}(R_{TE}+R_{TM})$ is used to analyze the sample properties, resulting in known values for the average reflectance and cos $2\Psi_S$, and Eq. 14 solved for cos $2\Psi_D$.

In either of the calibration methods, regions where cos $2\Psi_S \approx 0$ can be left out of the analysis and the value of cos $2\Psi_D$ interpolated using nearby wavelengths having known values of cos $2\Psi_D$. Alternately, the calibration procedure can use multiple known samples that have cos $2\Psi_D \approx 0$ in different wavelength regions.

Figure 13:
FIG. 13 illustrates a calibration/reference pad configuration for use with one embodiment of the present invention.

The calibration of polarization effects can be incorporated into the general calibration procedures described in U.S. Pat. Nos. 7,282,703, 7,511,265, 7,663,097, and 7,804,057, and U.S. patent application Ser. No. 12/592,641. In one embodiment, several calibration pads are provided for general reflectance calibration, as well as referencing specific types of film measurements, so that properties of samples can be analyzed without a specific calibration. For example, for most purposes the system may undergo a general reflectance calibration as described in U.S. Pat. Nos. 7,282,703, 7,511,265, 7,663,097, and 7,804,057, thereby determining $R_{Cal}$. For some specific measurements, such as measurements of thickness and composition of ultra-thin silicon oxynitride films on silicon substrates, a multiple relative reflectance measurement such as the one described in U.S. patent application Ser. No. 12/592,641 may also be used to simultaneously extract sample and reference parameters. The calibration for polarization effects described above can be incorporated into this general methodology, by placing one or more suitable calibration pieces having a grating pattern on the chuck, in addition to the uniform film reference pieces. Such an embodiment is illustrated in FIG. 13. Pads 1 and 2 are the standard calibration pads, Pad 3 might be another reference pad enabling specific types of relative reflectance measurements, and Pad 4 is a patterned sample consisting of a large-pitch grating of $SiO_2$ lines on silicon (for example). In principle, the calibration for polarization effects need only be performed once for a given system, but may be redone periodically as part of health monitoring of the tool, or to account for gradual changes in cos $2\Psi_D$.

Another embodiment uses a distinct referencing technique when measuring template samples in order to bypass the need for system calibration when measuring those structures. The nanoimprint template structure is usually a geometric structure etched directly into a bulk substrate piece, such as quartz or fused silica. As such, the substrate of the template patterned region is identical to an un-etched sample of the substrate material. Often, a template sample includes un-etched areas, suitable for self-referencing, nearby the patterned areas. In these cases, each template feature measurement may consist of the intensity measured from a patterned area followed by the intensity measured from a nearby un-patterned area. Rearranging the first part of Eq. 14 for calibrated reflectance gives $$\left(\frac{R'}{R_{Cal}}\right) = \left(\frac{I}{I_{Cal}}\right),$$ Eq. 20 where I is the intensity measured from the structured area, $I_{Cal}$ is the intensity measured from the un-etched region or reference piece, R' is the reflectance of the structured area, and $R_{Cal}$ is the reflectance of the bulk substrate. In this case, the regression analysis can be performed directly on the ratio $R'/R_{Cal}$, with the measured ratio determined from $I/I_{Cal}$. A quartz or fused silica reference piece can also be included in the generalized calibration methodology mentioned above, either to reference specific template measurements, or to be involved in the overall system calibration procedure. R' is defined as above, so that in the case that polarization effects are negligible, it is simply the sample reflectance at the patterned location.

One embodiment of the present invention may vary the integration time of a measurement depending on what is being measured. Longer integration times yield better signal-to-noise ratio, and therefore better base precision, but also expose the measured samples to higher doses of VUV radiation. This effect can be detrimental to measurements of samples that are sensitive to VUV exposure, such as photoresists. Conversely, quartz and fused silica are resilient to VUV exposure but have low reflectance values, so measurements of quartz or fused silica templates benefit from higher integration times than would be considered normal.

Meanwhile, the optimal integration time for the calibration procedures of U.S. Pat. Nos. 7,282,703, 7,511,265, 7,663,097, and 7,804,057 can be completely independent of these concerns, and it is desired that the optimal integration settings be used for calibration procedures regardless of how the sample is treated. Therefore, an embodiment of the present invention allows the calibration and sample integration times to be different. Additionally, the sample integration times can be attached to a specific sample measurement recipe, and can be different for different samples. So the calibration procedure and typical measurement settings may include an integration time, $t_1$, nanoimprint and uniform photoresist measurements use a different integration time, $t_2 < t_1$ so as to minimize VUV exposure effects, and quartz or fused silica template measurements would use a third integration time, $t_3 > t_1$, so as to maximize the signal for the template measurement.

The calibration procedure determines the reflectance of one or more calibration samples, $R_{Cal}$, which is then used to determine the system $I_0$ via $I_0 = I_{Cal}/R_{Cal}$ (Eq. 2 of U.S. Pat. No. 7,282,703). The sample reflectance is then determined from $R = I_r/I_0$ (Eq. 1 from U.S. Pat. No. 7,282,703). If the integration time $t_2$ used for the sample measurement is different from the time $t_1$ used for the calibration, the calibrated sample reflectance must be further modified by the factor $(t_1/t_2)$, so that $$R = \frac{I_r}{I_0} \cdot \frac{t_1}{t_2}.$$ Eq. 21

Figure 14:
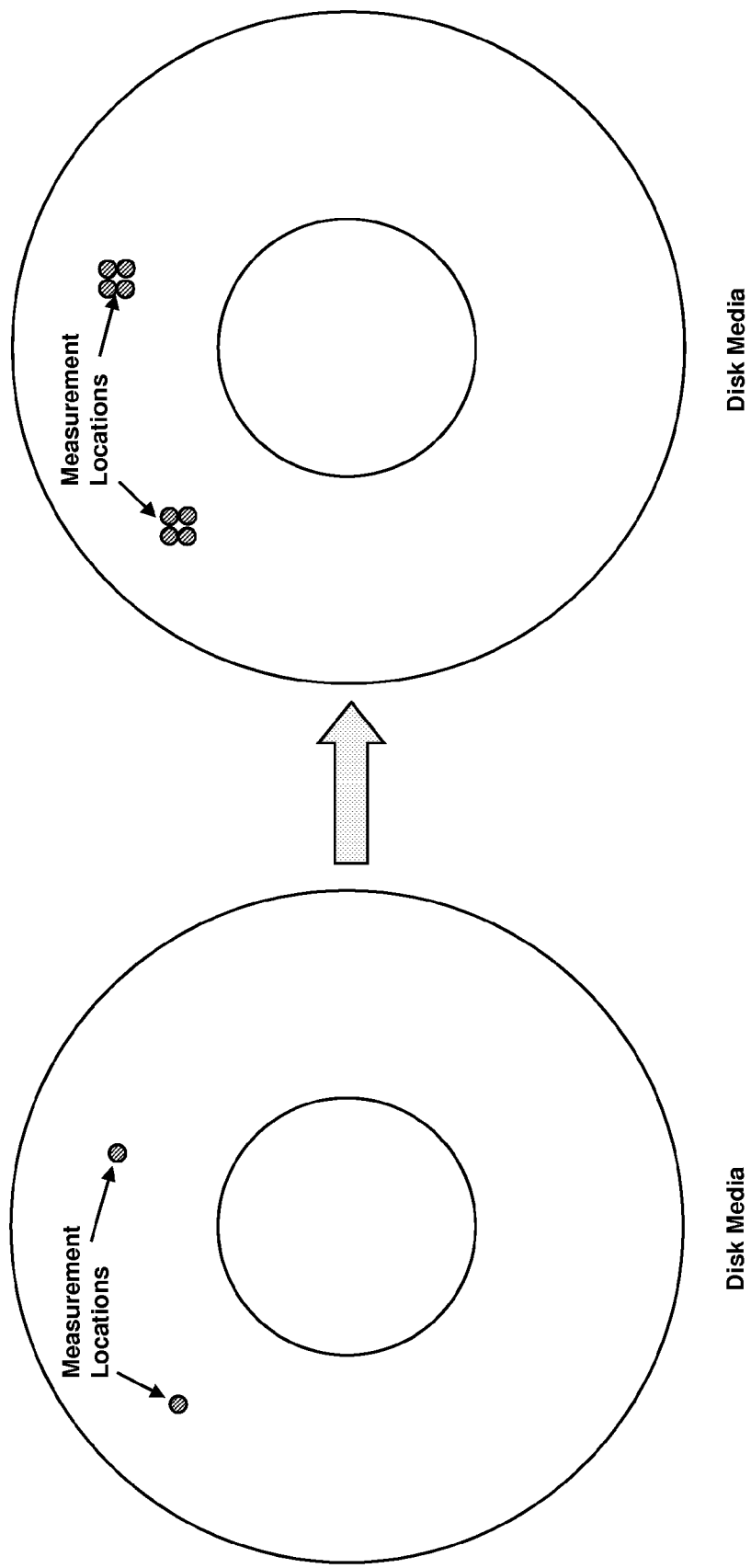
FIG. 14 illustrates replacing single point measurements with the average of a grid of closely spaced measurements, with the grid measurements having reduced integration time.

An embodiment of the present invention further minimizes VUV exposure of blanket or imprinted resist samples by replacing a single reflectance measurement with an average of several shorter measurements at different, but closely-spaced locations. In the present embodiment, it is possible to achieve measurement/exposure spots of ~30 μm diameter. Therefore, it is possible to average a number of non-overlapping measurements over a small enough region that the effects of sample non-uniformity on the average of the measurements is small. Each of these measurements is performed with a correspondingly shorter integration time. Each sample measurement is now an average of a cluster of shorter integration measurements over a small area. The advantage is that any given region on the film has been exposed for a shorter amount of time, while the signal quality remains essentially the same since the same total integration time is used. A mapping can be constructed that consists of groupings of points, the groupings being dispersed across the sample. The control software can average the reflectance from each grouping, and the average reflectance analyzed, or alternately perform a full measurement that analyzes each reflectance scan, and averages the measured results. This averaging can be done by hand in a spreadsheet after the measurement, but in a preferred embodiment is automatically handled by the metrology tool control software. FIG. 14 illustrates this method. The two measurements shown on the left are replaced by two four-point grids (for example), each having ¼ the total integration time of the original measurements. The user selects the location of the two points on the left, but indicates that the measurement integration should be divided over a grid of four points. The same information is obtained in the end—i.e. the difference in sample properties between the two locations—but with ¼ the total exposure to any given location on the sample.

While some embodiments of the present invention benefit from shorter calculation times than would be required for larger pitch structures, the reflectance calculation during the analysis step lends itself easily to distributed computing methods. The reflectance calculation requires a calculation of reflectance for many independent incident conditions including wavelength, polarization, and angle of incidence. For example, with a 3-angle distribution averaging, 120-800 nm un-polarized reflectance at 1 nm intervals, there are (680 incident wavelengths)×(3 incident angles)×(2 incident polarization states)=4080 independent calculations performed. These calculations can be distributed over any number of processor cores. Thus, some embodiments of the present invention benefit from a multi-threaded implementation whereby each full reflectance calculation is broken into sub-blocks of incident conditions and each sub-block assigned a separate computing thread. The number of threads can be equal to the number of physical processing cores, but need not be. Generally, the threads will be distributed evenly across the available processing cores. As long as the number of data points per thread remains relatively large (so overhead effects are minimized), the speed-up is approximately proportional to the number of physical processors available. At the current time, four-, eight-, and even 16-core workstation systems are available for reasonable cost, providing approximately 4, 8, or 16 times the calculation speed compared to similar single processor systems, and the cost-effectiveness of such a solution continues to trend upward with advances in computing technology. The computation can also be distributed across separate physical processors or processing machines. Referring to computing platform 1290 in FIG. 4, the distributed computing platform can be the same platform that controls the metrology tool, or computer 1290 can consist of two computer modules, one that handles the main control of the metrology tool, and a second distributed/multi-core system whose sole purpose is to perform reflectance calculations.

Accordingly, an embodiment of the present invention incorporates multi-threaded spectral calculations, where calculations for different incident conditions are distributed to different calculation threads, which now operate in parallel. In one embodiment, the data is distributed according to one calculation thread per physical processor. The physical processors can be CPU's on multiple separate machines, processor cores on a single or multiple multi-processor computer, or equivalent computation units on one or more Graphics Processing Units (GPU's). In another embodiment, a number of calculation threads that is a multiple of the number of physical processors/cores may be used, in order to further reduce latency overhead.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures. For example, equivalent elements may be substituted for those illustrated and described herein, and certain features of the invention may be utilized independently of the use of other features, all as would be apparent to one skilled in the art after having the benefit of this description of the invention.

What is claimed is:

1. An apparatus for measuring characteristics of a sample, the apparatus comprising:
   an optical metrology instrument comprising focusing optics for focusing light onto the sample and collecting the light reflected from the sample so as to record an optical response from nanoimprint structures on the sample, wherein the nanoimprint structures have an orientation that varies over a surface of the sample;
   a sample stage configured to support the sample; and
   at least one computer, which is connected to the metrology instrument and the sample stage and is configured to run a computer program which causes the sample stage to rotate the sample so as to present multiple different locations on the sample to the optical metrology instrument such that the orientation of the nanoimprint structures at the multiple different locations remains fixed with respect to a plane of the focusing optics of the metrology instrument in order to eliminate polarization effects,
   wherein the computer program causes the at least one computer to extract measured characteristics of the nanoimprint structures from a theoretical model of the sample
   while making use of the fixed orientation of the nanoimprint structures in extraction of the measured characteristics.

2. The apparatus of claim 1, wherein the computer program causes the sample stage to rotate the sample so that the orientation of the nanoimprint structures is fixed at an azimuth of $\phi=45°$ with respect to the plane of the focusing optics of the metrology instrument.

3. The apparatus of claim 1, wherein the optical metrology instrument is configured to operate at wavelengths below deep ultra-violet (DUV) wavelengths but not lower than vacuum ultra-violet (VUV).

4. The apparatus of claim 1, wherein the optical metrology instrument is configured to operate as a reflectometer.

5. The apparatus of claim 1, wherein the nanoimprint structures are formed on the sample such that they are circularly symmetric with respect to the center of the sample.

6. The apparatus of claim 1, wherein the sample stage comprises an r-θ stage.

7. The apparatus of claim 1, wherein the sample stage comprises an x-y-θ stage.

8. A method for measuring characteristics of a sample, the method comprising:
   operating an optical metrology instrument to focus light onto the sample and to collect the light reflected from the sample so as to record an optical response from nanoimprint structures on the sample, wherein the nanoimprint structures have an orientation that varies over a surface of the sample;
   rotating a sample stage that supports the sample so as to present multiple different locations on the sample to the optical metrology instrument such that the orientation of the nanoimprint structures at the multiple different locations remains fixed with respect to a plane of the light that is focused and collected by the metrology instrument in order to eliminate polarization effects; and
   running a computer program so as to cause at least one computer to extract measured characteristics from a theoretical model of the sample while making use of the fixed orientation of the nanoimprint structures in extraction of the measured characteristics.

9. The method of claim 8, wherein rotating the sample stage comprises orienting the sample so that the orientation of the nanoimprint structures is fixed at an azimuth of $\phi=45°$ with respect to the plane of the focused and collected light.

10. The method of claim 8, wherein operating the optical metrology instrument comprises focusing and collecting the light at wavelengths below deep ultra-violet (DUV) wavelengths but not lower than vacuum ultra-violet (VUV).

11. The method of claim 8, wherein operating the optical metrology instrument comprises collecting reflectometric data.

12. The method of claim 8, wherein the nanoimprint structures are formed on the sample such that they are circularly symmetric with respect to the center of the sample.

13. The method of claim 8, wherein the sample stage comprises an r-θ stage.

14. The method of claim 8, wherein the sample stage comprises an x-y-θ stage.

* * * * *